United States Patent
Suenaga et al.

(10) Patent No.: US 12,187,995 B2
(45) Date of Patent: Jan. 7, 2025

(54) METHOD AND APPARATUS FOR PRODUCING CONTAINER, CELL CULTURE VESSEL, METHOD FOR CULTURING CELLS, METHOD FOR PRODUCING CELL CULTURE VESSEL, AND APPARATUS FOR PRODUCING CELL CULTURE VESSEL

(71) Applicant: TOYO SEIKAN GROUP HOLDINGS CO., LTD., Tokyo (JP)

(72) Inventors: Ryo Suenaga, Yokohama (JP); Satoshi Tanaka, Yokohama (JP); Takahiko Totani, Yokohama (JP); Naoki Takahashi, Yokohama (JP)

(73) Assignee: TOYO SEIKAN GROUP HOLDINGS CO., LTD., Tokyo (JP)

( * ) Notice: Subject to any disclaimer, the term of this patent is extended or adjusted under 35 U.S.C. 154(b) by 17 days.

(21) Appl. No.: 17/839,142

(22) Filed: Jun. 13, 2022

(65) Prior Publication Data
US 2022/0306976 A1    Sep. 29, 2022

Related U.S. Application Data

(62) Division of application No. 16/322,012, filed as application No. PCT/JP2017/027229 on Jul. 27, 2017, now abandoned.

(30) Foreign Application Priority Data

Aug. 3, 2016 (JP) .................................. 2016-152493
Aug. 4, 2016 (JP) .................................. 2016-153701

(51) Int. Cl.
*C12M 1/00* (2006.01)
*B29C 35/00* (2006.01)
(Continued)

(52) U.S. Cl.
CPC ............ *C12M 23/14* (2013.01); *B29C 35/007* (2013.01); *B29C 59/02* (2013.01); *B65B 61/24* (2013.01);
(Continued)

(58) Field of Classification Search
CPC ...................................................... C12M 23/14
See application file for complete search history.

(56) References Cited

U.S. PATENT DOCUMENTS 3,338,794 A * 8/1967 Bendt .................... C12M 23/22
435/801
5,225,346 A * 7/1993 Matsumiya ............ C12M 23/22
435/304.2
(Continued)

FOREIGN PATENT DOCUMENTS

EP      0725134 A2 *  8/1996
JP      2003500265 A   1/2003
(Continued)

OTHER PUBLICATIONS

Translation of KR-100819860-B1 (Year: 2008).*
Translation of JP-2016039796-A (Year: 2016).*

*Primary Examiner* — John J DeRusso
(74) *Attorney, Agent, or Firm* — FISHERBROYLES, LLP; Roger L. Browdy; Ronni S. Jillions

(57) ABSTRACT

A vessel manufacturing method includes placing a bag-shaped, film-based vessel on a placement stage with concave portions formed on the stage, introducing fluid into the vessel placed on the stage, and pressing the vessel which is placed on the stage, by a pressing member while heating at least one of the stage and the pressing member. A cell culture vessel is also provided which includes a first vessel wall as a bottom wall and a second vessel wall. The first vessel wall is formed of a flat film having gas permeability. The second vessel wall is disposed in contact with a peripheral edge (Continued)

portion of the first vessel wall, and has a bulge shape protruding relative to the first vessel wall. The first vessel wall is flat at its section other than a region where the first vessel wall is in contact with at least a charge/discharge port.

10 Claims, 23 Drawing Sheets

(51) Int. Cl.
    *B29C 59/02*     (2006.01)
    *B65B 61/24*     (2006.01)
    *C12M 1/32*     (2006.01)
    *C12M 3/00*     (2006.01)

(52) U.S. Cl.
    CPC ............... *C12M 1/00* (2013.01); *C12M 3/00* (2013.01); *C12M 23/02* (2013.01); *C12M 23/12* (2013.01); *C12M 23/58* (2013.01); *C12M 47/04* (2013.01)

(56) References Cited

U.S. PATENT DOCUMENTS

| | | | |
|---|---|---|---|
| 6,759,003 | B1 | 7/2004 | Obara et al. |
| 2010/0027301 | A1 | 2/2010 | Hoyerby |
| 2010/0136680 | A1* | 6/2010 | Chono ............... A61J 1/10 435/325 |
| 2010/0187167 | A1 | 7/2010 | Reinbigler et al. |
| 2011/0020923 | A1* | 1/2011 | Lacey ............... C12M 23/34 435/304.2 |
| 2011/0151552 | A1* | 6/2011 | Jiang ............... C12M 23/14 435/289.1 |

FOREIGN PATENT DOCUMENTS

| | | | |
|---|---|---|---|
| JP | 2006055069 A1 | | 5/2006 |
| JP | 4780462 A | | 3/2008 |
| JP | 200848654 A | | 9/2009 |
| JP | 2011241159 A | | 12/2011 |
| JP | 2016039796 A | * | 3/2016 |
| JP | 2017184716 A | | 10/2017 |
| KR | 100819860 B1 | * | 4/2008 |
| WO | 2016208526 A1 | | 12/2016 |

* cited by examiner

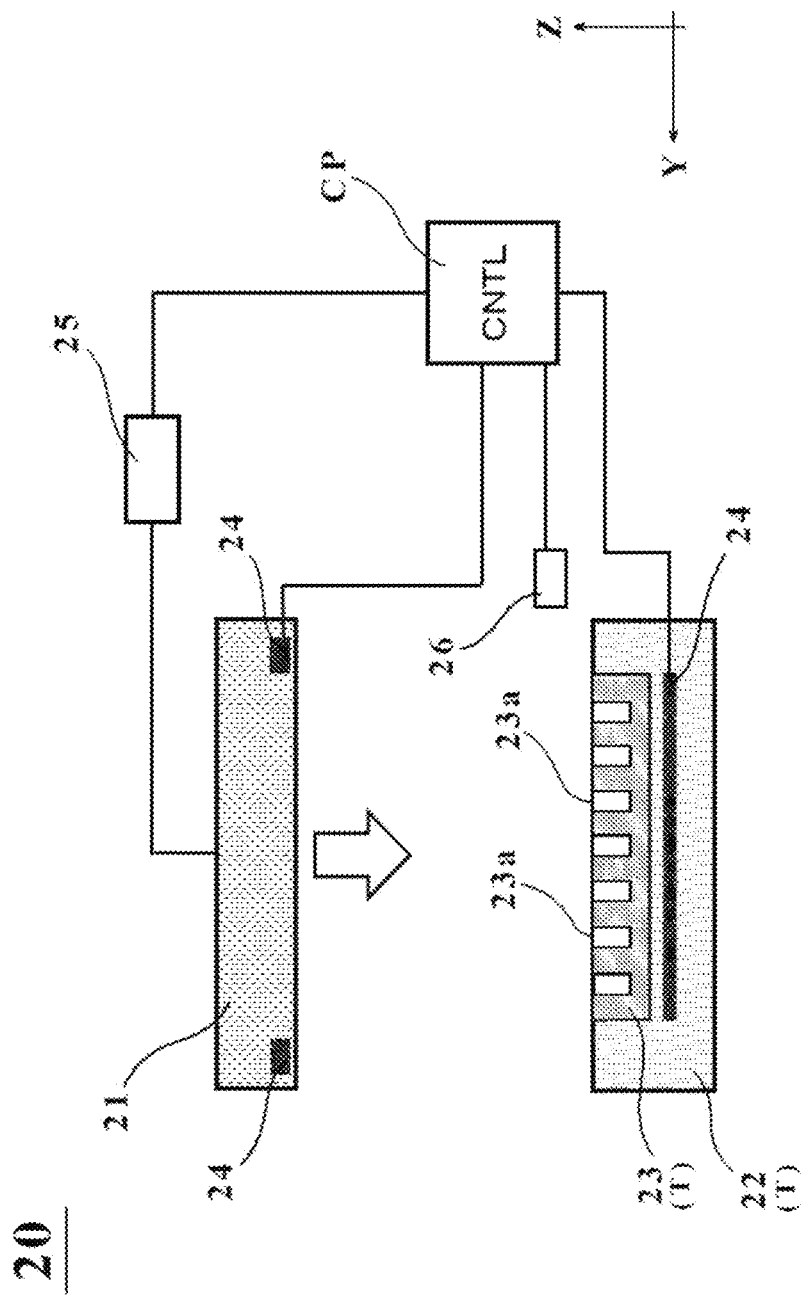

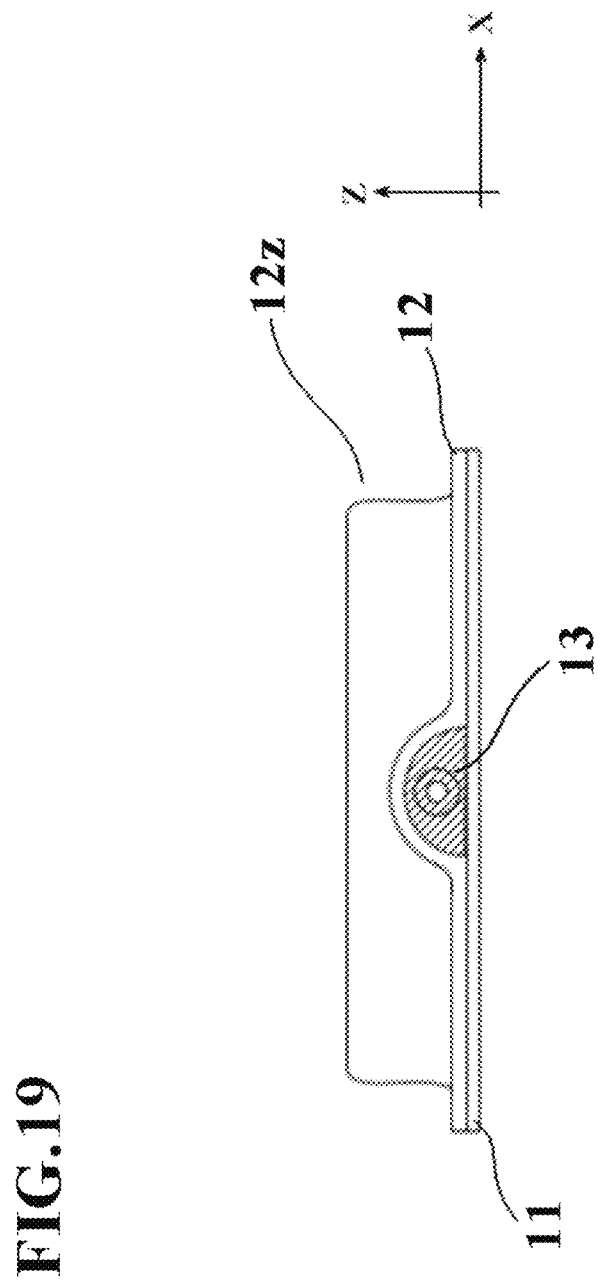

$50 cm^2$ BAG LIQUID QUANTITY 15 ml $50 cm^2$ BAG LIQUID QUANTITY 15 ml

METHOD AND APPARATUS FOR PRODUCING CONTAINER, CELL CULTURE VESSEL, METHOD FOR CULTURING CELLS, METHOD FOR PRODUCING CELL CULTURE VESSEL, AND APPARATUS FOR PRODUCING CELL CULTURE VESSEL

TECHNICAL FIELD

The present invention relates to a method and apparatus for manufacturing a vessel that can store various liquids and the like. The present invention also relates to techniques for culturing various cells, more specifically to a cell culture vessel that has gas permeability and can culture cells, a cell culturing method using the cell culture vessel, and a method for manufacturing the cell culture vessel.

BACKGROUND ART

In the modern medical field typified by gene therapy and regenerative therapy, it is practiced to conduct culture and differentiation induction of objective cells, which include tissues, microorganisms, viruses, and the like, under artificial environments. In recent years, there is a requirement especially for efficient and bulk culture and differentiation induction of the above-mentioned cells under artificial environments.

Now, upon culture and differentiation induction of cells, it is important to maintain the density of the cells in an appropriate range in culture medium from the viewpoint of supplying culture medium ingredients required for the proliferating cells, because the proliferation of the cells is inhibited by depletion of the culture medium ingredients, accumulation of metabolites of the cells themselves, and the like if the density of the cells in the culture medium increases with the proliferation of cells. On the other hand, it is also known that the formation of cell aggregates to certain extent is important for the efficient proliferation of the cells. Therefore, no efficient proliferation and differentiation induction of cells can be performed if the density of the cells in culture medium is too low.

From such background, a method has conventionally been used to repeat subculture such that the density of cells in culture medium remains appropriately.

As a method of such subculture, a well plate, a flask, or the like may be used as a culture vessel.

For example, PTL 1 discloses a technique that using a well plate, cells are added together with culture medium to individual wells to give an adequate cell density, followed by initiation of culture (see paragraph and the like). PTL 1 proposes to culture cells in bulk by allowing cells to sufficiently proliferate in each well, transferring the cells to a flask, adding fresh culture medium to the flask, transferring the cells to another flask of still greater capacity at a time point that the cells have proliferated to a predetermined population, and then conducting similar procedures.

Further, PTL 2 discloses a technique that a plurality of depressions is formed in a surface on one side of a flask-type culture vessel having a polyhedral shape such as a rectangular parallelepiped. According to PTL 2, aggregates of cells are first formed in the depressions, are transferred to a broader culture surface formed on an opposite side in the vessel, and are then allowed to proliferate into greater aggregates.

On the other hand, cells to be cultured by the above-described techniques can be classified into adherent culture cells and suspension culture cells depending on the existing form in the culture.

Adherent culture cells are culture cells that proliferate in adhesion to, for example, the bottom wall or the like of a culture vessel in which the cells are cultured. On these adherent culture cells, medium exchange is also performed as needed in addition to subculture that allows existing cultured cells to proliferate after transferring them to a new culture vessel.

For the above-described cell culture, culture vessels have heretofore been proposed as will be described hereinafter.

Known vessels for suitable use, for example, in laboratories include Petri dishes and culture flasks, which have a distortion-free flat bottom surface. Of these, Petri dishes can seal their insides with a lid. Vent-type lids include ribs, and allow selection of a venting/non-venting position. On the other hand, culture flasks which have a flat bottom surface like Petri dishes also have a culture surface of excellent uniformity and smoothness, and therefore have a merit that a good field of vision can be obtained upon microscopic observation.

As opposed to open-system cell culture that uses a Petri dish or culture flask, closed-system cell culture that conducts culture of cells in a tightly-sealed space is also known. In such closed-system cell culture, cell culture bags formed of flexible resin are suitably used from a need for suppressing any contamination risk while ensuring transparency and gas permeability.

Nonetheless, general cell culture bags involve a problem that their bottom surfaces as culture surfaces become no longer flat when culture liquid is charged, and therefore, tray-shaped cell culture vessels as disclosed, for example, in PTL 3 have been proposed. Described specifically, the tray-shaped cell culture vessel disclosed in PTL 3 has a configuration that a first vessel wall is transparent and includes a recessed part having a single flat bottom surface and a flange portion formed at a peripheral edge portion of the recessed part and a second vessel wall has gas permeability and deformable flexibility.

CITATION LIST

Patent Literature

[PTL 1]
JP 2011-241159 A
[PTL 2]
JP 2006-055069 A
[PTL 3]
JP 4780462 B

SUMMARY

Technical Problems

When conducting subculture as described above, however, it is necessary to repeat pipetting many times upon seeding cells in the individual wells of a well plate and also upon transferring the cells from the well plate to flasks. Therefore, cumbersome work is unavoidable. In addition, the cells have to be transferred into new culture vessels such as flasks upon every subculture. This requirement leads not only to cumbersome work, but also to a higher risk of contamination with unintentional bacteria or virus.

With a flask-type culture vessel as in PTL 2, gas exchange is performed only when a plug which closes up an opening portion is removed from the opening portion and the opening portion is opened. Accordingly, oxygen cannot be supplied in a sufficient quantity to cells under culture, and moreover a risk of contamination cannot be avoided upon gas exchange. Furthermore, the use of flask-type culture vessels, the capacities of which are limited, is unrealistic for bulk culture of cells on a non-laboratory scale.

Also concerning cell culture vessels, there are still many problems to be resolved or alleviated as will be described hereinafter although the flatness of a culture surface can be certainly ensured to some extent according to PTL 3.

Specifically, in adherent culture cells typified, for example, by iPS cells and the like, the degree of proliferation of the cells depends on the extent of an area, so that mere assurance of a flat culture surface alone is not sufficient and there is a need for making a culture surface as flat and wide as possible. Cells especially for use in regenerative therapy or the like are very precious, and a great deal of time and expense is required for their culture. High efficiency is also required accordingly.

In addition, culture medium (e.g., culture liquid) needed for cell culture is very expensive, so that there is a potential need to efficiently use the culture medium in as small an amount as possible. Therefore, a culture surface that is required for the culture of cells has to be formed as a flat uppermost layer over as wide a range as possible, and also has to allow culture liquid to flow to every corner of the culture surface while using the culture liquid in a relatively small quantity.

It is also desired to make the thickness dimension of the culture liquid even over a wide range such that the cells settled on a bottom surface after seeding are evenly distributed in terms of cell density and the nutrients of the culture liquid are evenly supplied to all the cells.

However, the cell culture vessels of the conventional types, including that of PTL 3, include absolutely no recognition or suggestion on the above-described problems.

With a view to resolving, as an example, at least one of the above-described problems, the present invention has as objects thereof the provision of a method and apparatus for manufacturing a cell culture vessel, which enables efficient culture and differentiation induction of cells in the same vessel with a reduced risk of contamination while appropriately maintaining the density of cells during the culture.

In addition, the present invention also has as other objects thereof the provision of a cell culture vessel, which ensures to provide a flat culture surface over a wide range and allows culture liquid to flow with an even thickness dimension to every corner of the culture surface even if the culture liquid is in a small quantity, a cell culture method using the cell culture vessel, and a method for manufacturing the cell culture vessel.

Solution to Problems

To achieve the former objects described above, in an aspect of the present invention, there is provided a method for manufacturing a vessel. The method includes the steps of placing a bag-shaped, film-based vessel on a placement stage with concave portions formed thereon, and a step of pressing the bag-shaped, film-based vessel which is placed on the placement stage, by a pressing member which opposes the placed bag-shaped, film-based vessel, while heating at least one of the placement stage and the pressing member.

In another aspect of the present invention, there is also provided an apparatus for manufacturing a vessel. The apparatus includes a placement stage with concave portions formed on a placement surface thereof on which a bag-shaped, film-based vessel is to be placed, a fluid inlet device configured to introduce fluid into the bag-shaped, film-based vessel placed on the placement surface, a pressing member arranged movably up and down relative to the placement surface and configured to press the bag-shaped, film-based vessel into which the fluid has been introduced, and a heating device configured to heat at least one of the placement stage and the pressing member.

To achieve the latter objects described above, in a further aspect of the present invention, there is also provided a cell culture vessel. The cell culture vessel includes a first vessel wall as a bottom wall, the first vessel wall being formed of a flat film having gas permeability, a second vessel wall disposed in contact with a peripheral edge portion of the first vessel wall, and having a bulge shape protruding relative to the first vessel wall on a side inner than the peripheral edge portion, and a charge/discharge port communicating to a culture space surrounded by the first vessel wall and the bulge shape of the second vessel wall. The first vessel wall is flat at a section thereof other than a region thereof where the first vessel wall is in contact with at least the charge/discharge port.

In a still further aspect of the present invention, there is also provided a method for culturing cells by using the cell culture vessel according to the further aspect. The method includes placing the cell culture vessel with the first vessel wall located downward relative to the second vessel wall, and charging the cells and culture medium into the cell culture vessel through the charge/discharge port.

In a yet further aspect of the present invention, there is also provided a method for manufacturing a cell culture vessel. The method includes the steps of placing a first vessel wall which is formed of a film having gas permeability, and a second vessel wall which is disposed opposite the first vessel wall, in a superimposed state on a placement stage, pressing the first vessel wall and the second vessel wall at peripheral edge portions thereof by a restraint member in a state that the second vessel wall is maintained free from being pressed at a central section thereof, introducing fluid between the first vessel wall and the second vessel wall with the peripheral edge portions thereof pressed by the restraint member, and heating at least the pressing member while pressing the second vessel wall at the central section thereof by a pressing member.

In a still yet further aspect of the present invention, there is also provided an apparatus for manufacturing a cell culture vessel including a first vessel wall formed of a flat film and a second vessel wall disposed in contact with a peripheral edge portion of the first vessel wall and having a bulge shape protruding relative to the first vessel wall. The apparatus includes a placement stage on which the first vessel wall is to be placed, a fluid inlet device configured to introduce fluid into a space between the first vessel wall placed on the placement stage and the second vessel wall, a pressing member arranged movably up and down relative to the placement stage and configured to press the second vessel wall with the fluid introduced in the space, a heating device configured to heat the pressing member, and a restraint member arranged opposite the placement stage and configured to restrain the second vessel wall which is placed on the placement stage, at a peripheral edge portion thereof. The fluid is introduced into the space between the first vessel wall and the second vessel wall by the fluid inlet device while heating the pressing member by the heating device with the second vessel wall restrained at the peripheral edge portion thereof by the restraint member.

Advantageous Effects of Invention

According to the present invention, a vessel with one or more depressions formed in an inner surface thereof can be efficiently manufactured. It is also possible to efficiently manufacture a vessel which, especially if applied for use in cell culture, can appropriately maintain the density of cells during culture to suppress depletion of culture medium ingredients needed for their proliferation and can also suppress any contamination risk with contaminants and the like.

According to the present invention, it is also possible to ensure the provision of a flat culture surface over a wide range by the flat first vessel wall as the bottom wall, and further to allow culture liquid to flow to every corner of the culture surface by the second vessel wall having the bulge shape even if the culture liquid is in a small quantity. In addition, bulk culture of high-quality cells is feasible with the density of cells appropriately maintained during the culture, without the occurrence of depletion of culture medium ingredients needed for their proliferation, and with a suppressed contamination risk.

BRIEF DESCRIPTION OF DRAWINGS

FIGS. 1A to 1C are explanatory diagrams depicting an outline of a cell culture vessel 1 according to a first embodiment, in which FIG. 1A is a plan view, FIG. 1B is a side view, and FIG. 1C is a bottom view.

FIG. 2 is a schematic diagram depicting an outline configuration of a manufacturing apparatus 20 for the cell culture vessel in the first embodiment.

FIG. 19 is a front view of the cell culture vessel 10 according to the fifth embodiment.

DESCRIPTION OF EMBODIMENTS

Figure 1A:
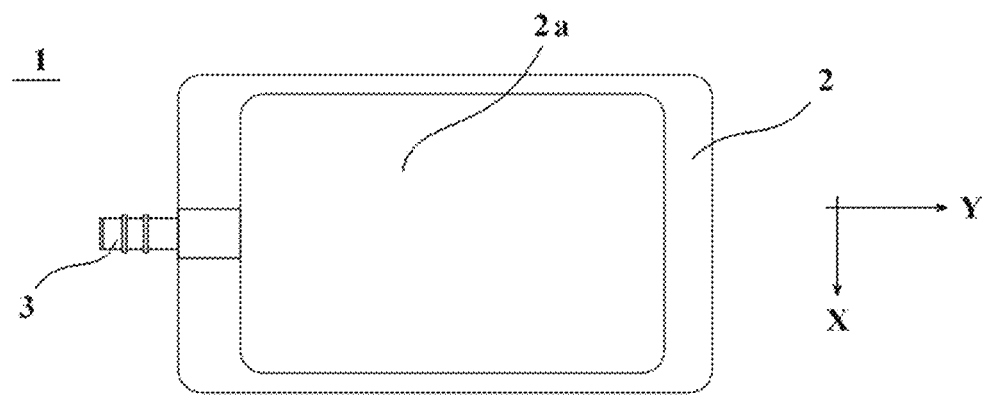

Referring to the drawings as needed, a specific description will hereinafter be made about methods and apparatus for manufacturing vessels in the present invention, which are to be applied for use in culture of cells. For the sake of convenience of description, an X-direction, an Y-direction, and a Z-direction will be individually defined subsequently herein, but these directions are not intended to limit or restrict the scope of right of the present invention.

First Embodiment

[Cell Culture Vessel 1]

Figure 1B:
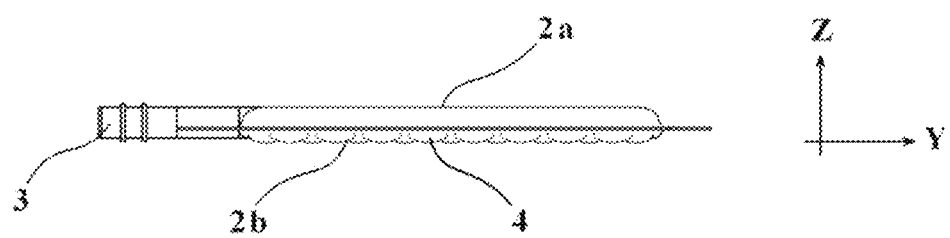
Figure 1C:
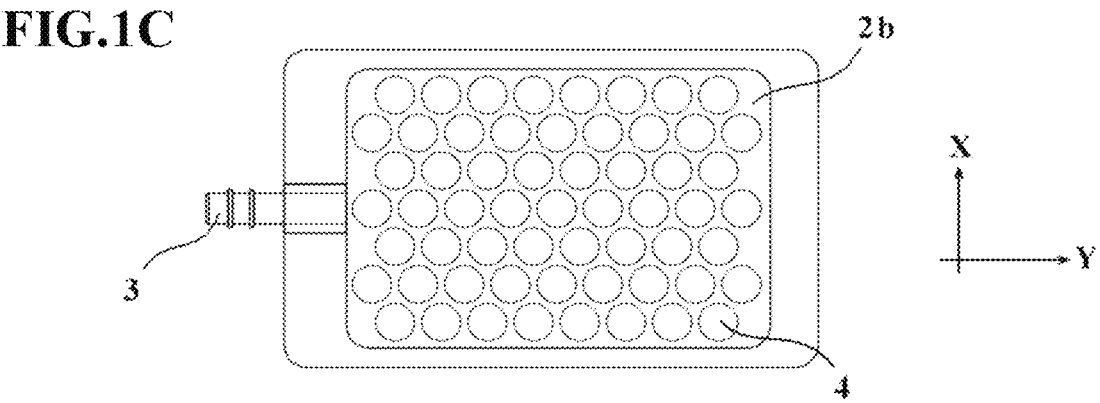

A cell culture vessel 1 depicted in FIGS. 1A to 1C has a plurality of depressions in a bottom wall, and includes a vessel main body 2 and a charge/discharge port 3. The vessel main body 2 is formed of a known plastic film having gas permeability, and the charge/discharge port 3 is formed of a tubular member through which culture medium, cells, and the like can flow.

The vessel main body 2 is sealed at a peripheral edge portion thereof, has a bulge shape protruding in a plateau shape on the side of a top wall 2a thereof, and is formed such that the top wall 2a formed as a flat wall is inclined at an edge thereof to extend to the peripheral edge portion. In addition, the vessel main body 2 includes, in a bottom wall 2b thereof, depressions 4 to be used as cell culture portions. At least one depression is required although the plurality of depressions 4 is included in this embodiment. No particular limitation is imposed on the size of the vessel main body 2. Preferably, however, the vessel main body 2 may be set, for example, at 20 to 1000 mm in length and 20 to 1000 mm in width.

Further, the gas permeability of the plastic film that forms the vessel main body 2 may preferably be 5000 mL/m²·day·atm or more in terms of oxygen permeability as measured at a test temperature of 37° C. in accordance with JIS K 7126 Gas Permeability Testing Method.

No particular limitation is imposed on a material to be used in the plastic film forming the above-described vessel main body 2, insofar as the material has desired gas permeability. Illustrative are thermoplastic resins such as polyethylene, polypropylene, ethylene-vinyl acetate copolymer, polyesters, silicone-based elastomers, polystyrene-based elastomers, and tetrafluoroethylene-hexafluoropropylene copolymer (FEP). Such a material may be used as a single layer, or such a material or two or more different ones of such materials may be used as a laminate. Taking into account the thermal fusion bondability upon sealing the peripheral edge portion, however, the plastic film may preferably have a layer that functions as a sealant layer.

In addition, the plastic film may preferably have transparency at a part or the entire part thereof such that the status of progress of the culture of cells, the conditions of cells, and the like can be seen.

The depressions 4 disposed in the bottom wall 2b of the vessel main body 2 may preferably have an opening diameter (diameter) of such a dimension that the cells under culture in the depressions 4 can remain in the same depressions 4 while being suppressed from moving around in the vessel main body 2. The opening diameters of the respective depressions 4 may be set equal among all the depressions. As an alternative, the depressions 4 disposed in the bottom wall 2b may include two or more kinds of depressions different in opening diameter, for example, by dividing the bottom wall 2b into a plurality of section and making the opening diameters of the depressions different from one section to another. Further, in the cell culture vessel 1 depicted in FIGS. 1A to 1C, the depressions 4 are formed in a hemispherical shape to facilitate gathering of the cells in bottom parts of the depressions 4, although the depressions 4 are not limited to such a hemispherical shape.

In order to avoid stagnation of cells at regions of the bottom wall 2b other than the depressions 4, the occupation area of the depressions 4 in the bottom wall 2b may preferably be set as large as possible to the extent that the formability is not impaired. Specifically, the occupation area of the depressions 4 may preferably account for 30 to 90% based on the area of the bottom wall 2b. Concerning the array of the depressions 4, the depressions 4 may preferably be arrayed in a staggered pattern as depicted in FIG. 1C such that the depressions 4 have as large an occupation area as possible on the bottom wall 2b, but may also be arrayed in a grid pattern as needed.

As mentioned above, the charge/discharge port 3 is formed of a tubular member through which culture medium, cells, and the like can flow. Using, for example, a thermoplastic resin such as polyethylene, polypropylene, polyvinyl chloride, a polystyrene-based elastomer, or FEP, the tubular member that forms the charge/discharge port 3 can be formed into a predetermined shape by injection molding, extrusion, or the like.

To perform culture of cells by using the above-described cell culture vessel 1, the cells to be cultured are charged together with culture medium into the vessel main body 2 through a liquid supply tube connected to the charge/discharge port 3 while maintaining a closed system. Then, the cells charged in the vessel main body 2 settle through the culture liquid and gather in bottom parts of each depression 4.

[Manufacturing Apparatus for Cell Culture Vessel 1]

Figure 3B:
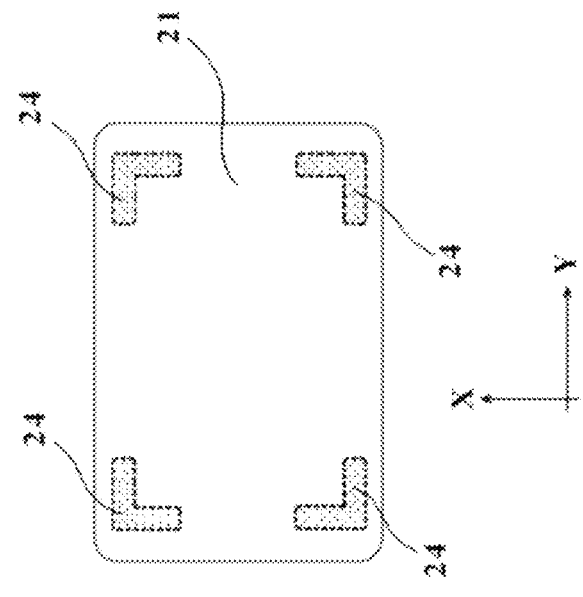
FIGS. 3A and 3B are schematic diagrams illustrating the structures of a placement stage T and a pressing member 21, respectively, in the manufacturing apparatus 20 for the cell culture vessel in the first embodiment.
Figure 3A:
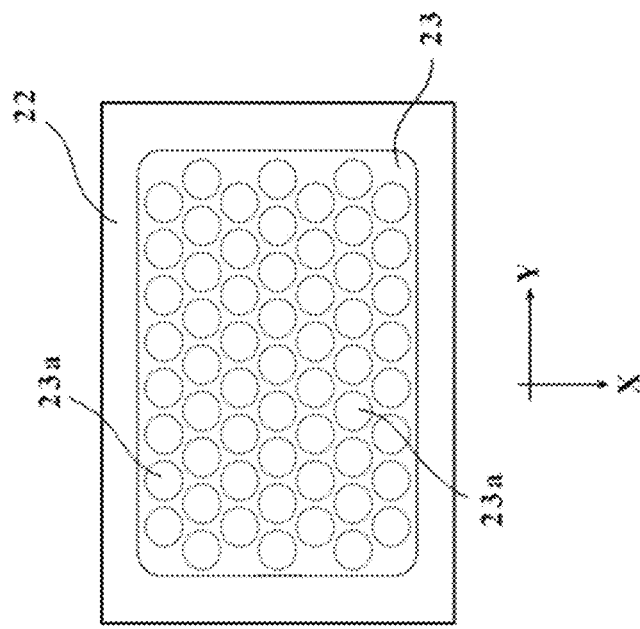

With reference to FIG. 2 and FIGS. 3A and 3B, a description will next be made about a manufacturing apparatus 20 for the cell culture vessel in this embodiment.

As depicted in FIG. 2, the manufacturing apparatus 20 for the cell culture vessel is configured including a pressing member 21, a placement stage T, a heating device 24, and a fluid inlet device 26.

The pressing member 21 has a function to press a bag-shaped, film-based vessel 1a (see FIG. 4A) placed on a placement surface of the placement stage T. The term "bag-shaped, film-based vessel" means a preform to be subsequently formed into the cell culture vessel 1, specifically a vessel on which neither the depressions 4 nor the bulge shape has been formed yet. The pressing member 21 is formed, for example, from a metal such as aluminum or iron or a resin such as a plastic. As illustrated in FIG. 3B, the external shape of the pressing member 21 is, for example, rectangular, and is dimensioned, for example, so that the pressing member 21 becomes a little greater than the external shape of the bag-shaped, film-based vessel 1a placed on the placement surface. The size of the pressing member 21 in the directions of an X-Y plane is required as a minimum to have at least an area of a size such that the above-described bulge shape can be pressed at a flat top surface thereof, and if there are restraint members 29 to be described in a fourth embodiment, for example, is restricted to the inner side of the restraint members 29.

The pressing member 21 is connected to a drive mechanism 25, and is arranged movably up and down relative to the placement surface via the drive mechanism 25. Upon manufacturing the below-described cell culture vessel, the pressing member 21 presses the bag-shaped, film-based vessel 1a placed on the placement surface with a fluid introduced therein. No particular limitation is imposed on the drive mechanism 25, and a known drive mechanism such as a fluid cylinder mechanism, a ball screw mechanism, or an electric motor mechanism can be applied.

The placement stage T is a support stage with concave portions formed on the placement surface on which the bag-shaped, film-based vessel 1a is to be placed, and has a function to support the bag-shaped, film-based vessel 1a. The placement stage T in this embodiment includes plural concave portions formed corresponding to the depressions 4 of the above-described cell culture vessel 1. If the cell culture vessel 1 has a single depression 4, however, the placement stage T also has a single concave portion. In other words, one or more concave portions are formed on the placement stage T in this embodiment.

The placement stage T in this embodiment is configured of two members, that is, a placement stage main member 22 and a vessel support member 23.

The placement stage main member 22 is formed from a material having a lower thermal conductivity than the vessel support member 23. As depicted in FIG. 2 and illustrated in FIG. 3A, a recessed section is formed in an upper wall of the placement stage main member 22, and the vessel support member 23 is accommodated in the recessed section. The placement stage main member 22 also has a function to support the bag-shaped, film-based vessel 1a at a peripheral edge portion thereof when the bag-shaped, film-based vessel 1a is placed on the placement stage T. In other words, the placement stage main member 22 takes a function as the placement surface that supports the bag-shaped, film-based vessel 1a at the peripheral edge portion thereof.

The vessel support member 23 is formed from a material having a higher thermal conductivity than the placement stage main member 22. In this embodiment, aluminum is used in the vessel support member 23, while cast iron is used in the placement stage main member 22. As in Modification 3 depicted in FIG. 16, which will be described later, and the like, the placement stage main member 22 and the vessel support member 23 may be formed from the same material, and are not necessarily required to be different in thermal conductivity.

As illustrated in FIG. 3A, a plurality of concave portions 23a are formed on an upper surface of the vessel support member 23 (the placement surface on which the bag-shaped, film-based vessel 1a is to be placed). These concave portions 23a correspond to the depressions 4 of the above-described cell culture vessel 1. Therefore, the concave portions 23a may have the same opening diameter among the entirety of thereof. As an alternative, the concave portions 23a may include two or more kinds of concave portions 23a different in opening diameter, for example, by dividing the placement surface of the vessel support member 23 into a plurality of sections and making the opening diameters of the concave portions 23a different from one section to another.

Further, the concave portions 23a are formed in a hemispherical shape, although the concave portions 23a are not limited to such a hemispherical shape and may be in a columnar shape or the like.

Concerning the array of the concave portions 23a, the concave portions 23a may preferably be arrayed in a staggered pattern as depicted in FIG. 3A such that the concave portions 23a have as large an occupation area as possible, but may also be arrayed in a grid pattern as needed.

The heating device 24 has a function to heat at least one of the placement stage T and the pressing member 21. As the heating device 24 in this embodiment, resistance heating devices such as, for example, Nichrome wires may be exemplified. The heating device 24 can be embedded in each of the pressing member 21 and the placement stage main member 22 or vessel support member 23.

Described more specifically, one of the heating devices 24 in this embodiment is embedded inside the placement stage main member 22 (see FIG. 2), and the other heating device 24 is embedded in the pressing member 21 on a pressing side thereof, in other words, on the side of a bottom surface thereof (see FIG. 3B).

Of these heating devices 24, the heating device 24 embedded in the placement stage main member 22 is arranged under the entire surface of the placement stage main member 22 such that the heating device 24 corresponds to the bottom wall of the bag-shaped, film-based vessel 1a. As a consequence, heat can be conducted to every one of the plurality of the depressions 4 formed on the bottom wall 2b.

On the other hand, the heating device 24 embedded in the pressing member 21 is not arranged widely inside the bottom surface of the pressing member 21, but is arranged corresponding to positions as edges of the top wall 2a of the above-described cell culture vessel 1. As a consequence, it is possible to avoid wasteful heating and to perform efficient heating to necessary locations.

The fluid inlet device 26 has a function to introduce fluid into the bag-shaped, film-base vessel 1a placed on the placement surface of the placement stage T. The fluid inlet device 26 in this embodiment introduces fluid into the bag-shaped, film-base vessel 1a through the above-described charge/discharge port 3. As the fluid to be introduced by the fluid inlet device 26, liquid or gas can be exemplified. As the liquid, pure water or the like is applied specifically. As the gas, cleaned air (clean air) or inert gas such as nitrogen is applied. Of these, from the viewpoint of handling and processing ease, clean air is applied in this embodiment.

In addition, the fluid inlet device 26 in this embodiment also has a function to control the supply pressure of the fluid to be introduced into the bag-shaped, film-based vessel 1a. Owing to this function, the above-described supply pressure can be maintained constant or can be varied before and after the bag-shaped, film-based vessel 1a is pressed by the pressing member 21.

The fluid inlet device 26 may have a function to control the supply flow rate of the fluid instead of the above-described function to control the supply pressure of the fluid. Owing to this function, control of the flow rate of the fluid to be supplied into the bag-shaped, film-based vessel 1a makes it possible to easily perform control of the amount of protrusion in the above-described bulge shape of the vessel main body 2. More specifically, if the vessel main body 2 is to be formed in a bulge shape having a small amount of protrusion (in other words, a vessel is to be formed for a small liquid thickness dimension or a small liquid quantity, for example), the fluid inlet device 26 may control to decrease the supply flow rate of the fluid to be supplied into the bag-shaped, film-based vessel 1a. If the vessel main body 2 is to be formed in a bulge shape having a large amount of protrusion (in other words, a vessel is to be formed for a large liquid thickness dimension or a large liquid quantity), conversely, the fluid inlet device 26 may control to increase the supply flow rate of the fluid to be supplied into the bag-shaped, film-based vessel 1a.

The manufacturing apparatus 20 for the cell culture vessel in this embodiment may further include a control unit CP. This control unit CP has a function to control operation of the above-descried heating devices 24, drive mechanism 25, and fluid inlet device 26. Specifically, a computer that includes an undepicted memory and CPU can be exemplified as the control unit CP. The manufacturing apparatus 20 for the cell culture vessel is not necessarily required to include the control unit CP, and may be remote controlled from a remote place via a network such as LAN.

[Manufacturing Method for Cell Culture Vessel 1]

Figure 4A:
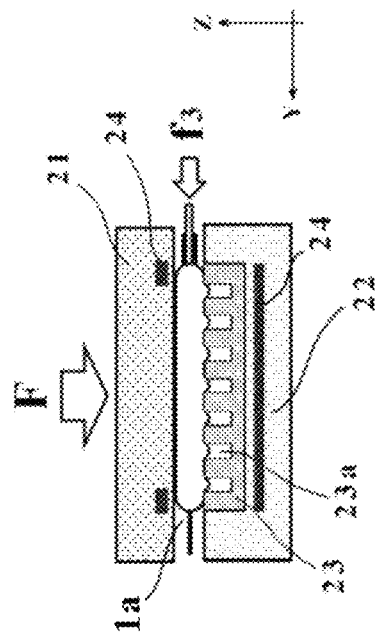
FIGS. 4A through 4D are state transition diagrams of the manufacturing apparatus 20 for the cell culture vessel in the first embodiment.
Figure 4B:
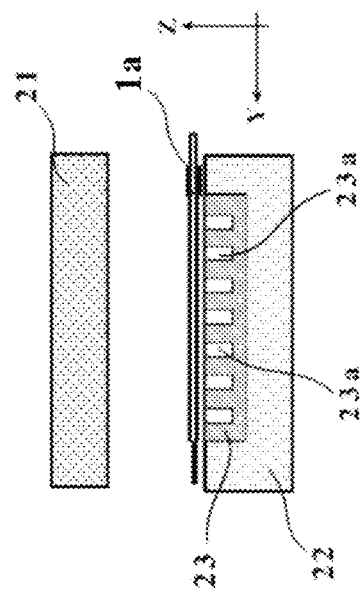
Figure 4C:
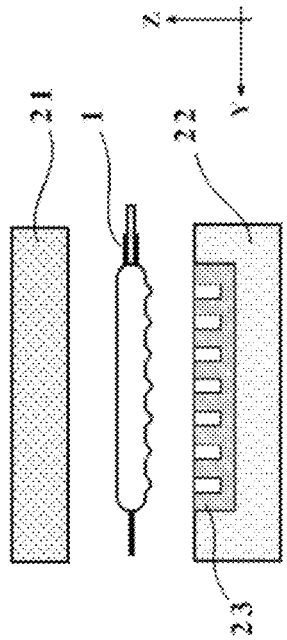
Figure 4D:
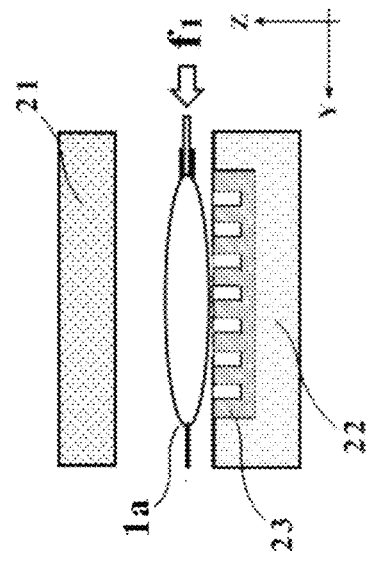
Figure 5:
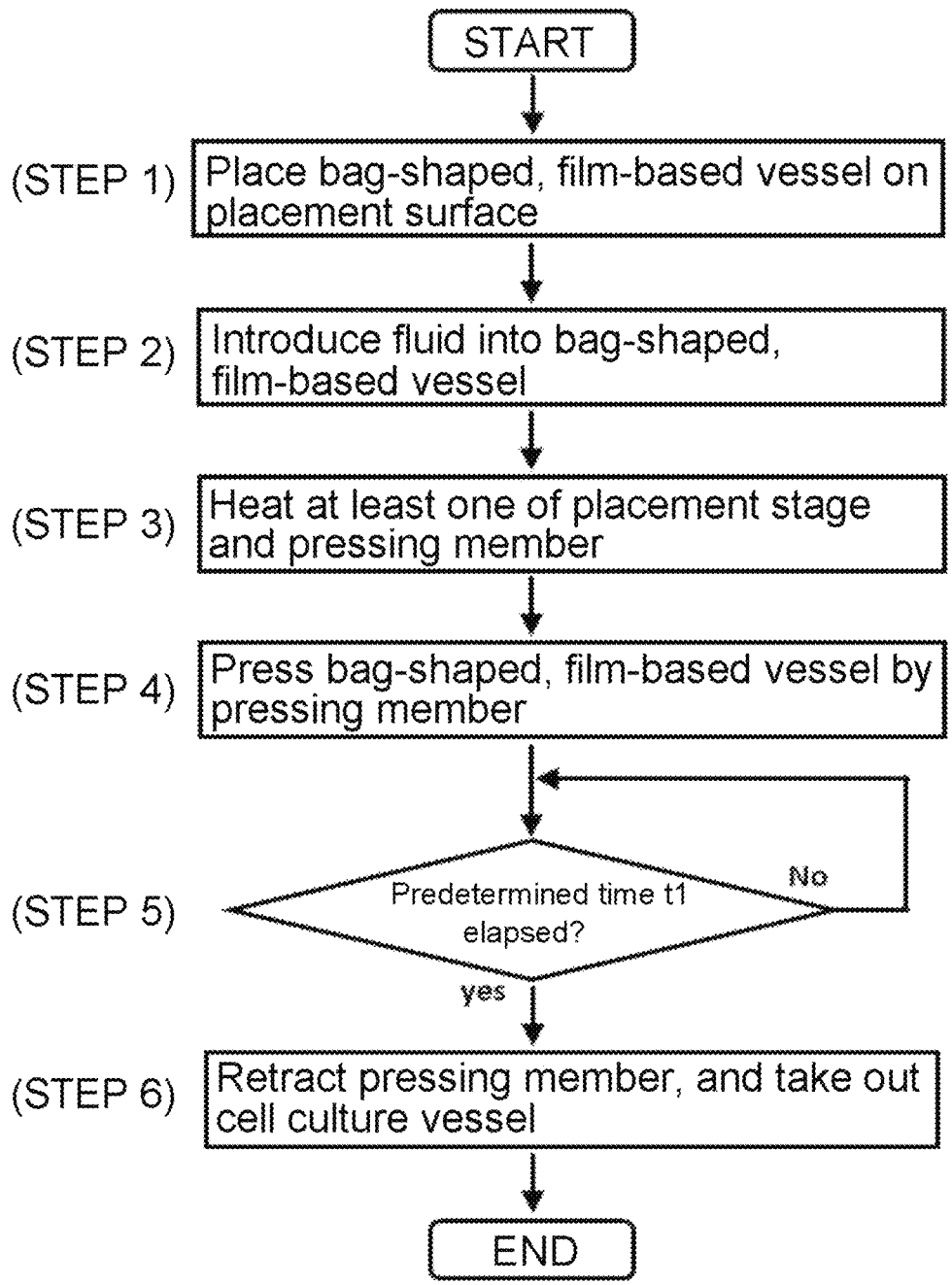
FIG. 5 is a flow chart illustrating a manufacturing method for the cell culture vessel in the first embodiment.

With reference to FIGS. 4A through 4D and FIG. 5, a description will next be made about a manufacturing method for the cell culture vessel in this embodiment. FIGS. 4A through 4D are state transition diagrams of the manufacturing apparatus 20 for the cell culture vessel in this embodiment, and FIG. 5 is a flow chart illustrating the manufacturing method for the cell culture vessel, the manufacturing method also corresponding to the state transition diagrams of FIGS. 4A through 4D.

As illustrated in FIG. 4A and indicated in step 1 of FIG. 5, the bag-shaped, film-based vessel 1a is first placed on the placement stage T with the plurality of concave portions 23a formed thereon. At this time, the bag-shaped, film-based vessel 1a may preferably be placed so that its peripheral edge portion is supported on the placement stage main member 22.

After the bag-shaped, film-based vessel 1a has been placed in step 1, fluid is introduced into the bag-shaped, film-based vessel 1a as illustrated in FIG. 4B and indicated in step 2 of FIG. 5. At this time, the fluid inlet device 26 supplies clean air mentioned above, at a supply pressure f1 in this embodiment. As also mentioned above, the fluid inlet device 26 may perform supply control of the clean air based on the supply flow rate instead of the supply pressure.

Next, as illustrated in FIG. 4C and indicated in steps 3 and 4 of FIG. 5, while heating at least one of the placement stage T and the pressing member 21 opposing the bag-shaped, film-based vessel 1a placed on the placement stage T, the placed bag-shaped, film-based vessel 1a is pressed by the pressing member 21. In other words, after the fluid has been introduced into the bag-shaped, film-based vessel 1a, the pressing member 21 is brought close to the placement stage T to press the bag-shaped, film-based vessel 1a under a pressing force F.

The heating temperature at this time may preferably be set at such a level as making the bag-shaped, film-based vessel 1a soft without melting, for example, at substantially 80° C.

It is not required to perform step 3 and step 4 in this order. For example, after pressing the bag-shaped, film-based vessel 1a by the pressing member 21, at least one of the placement stage T and the pressing member 21 may be heated by the heating device 24. At this time, the fluid inlet device 26 supplies clean air, which has been cleaned as mentioned above, at a supply pressure f3 in this embodiment.

In this embodiment, the heating devices 24 are individually arranged in the pressing member 21 and the placement stage T. As a consequence, the regions of the bag-shaped, film-based vessel 1a, which will be formed into the depressions 4 subsequently, can be heated by the heating device 24 arranged in the placement stage T, and the section of the bag-shaped, film-based vessel 1a, which will be formed into the bulge shape subsequently, can be efficiently heated by the heating device 24 arranged in the pressing member 21.

Subsequent to the initiation of the heating and pressing to the bag-shaped, film-based vessel 1a in steps 3 and 4, a determination is made, as indicated in step 5 of FIG. 5, as to whether or not a predetermined time t1 has elapsed.

This predetermined time t1 is not particularly limited insofar as the above-described depressions 4 and bulge shape are formed, and may be, for example, substantially several seconds to several minutes.

As appreciated from the above, it is possible in this embodiment to form the bag-shaped, film-based vessel 1a into a bulge shape with an upwardly protruding top wall by introducing fluid into the bag-shaped, film-based vessel 1a while maintaining the pressing member 21 apart by a predetermined distance from the placement stage T.

In these steps 3 to 5, the fluid inlet device 26 may be configured to control the supply pressure of fluid before and after the above-described pressing by the pressing member 21. More specifically, the pressure inside the bag-shaped, film-based vessel 1a rises with the pressing of the bag-shaped, film-based vessel 1a by the pressing member 21. However, the control of the supply pressure of the fluid by the fluid inlet device 26 can suppress the pressure inside the bag-shaped, film-based vessel 1a from changing excessively. In other words, the fluid inlet device 26 may be configured to maintain the supply pressure of the fluid at a constant value (f1=f3) under control by the control unit CP such that the internal pressure of the bag-shaped, film-based vessel 1a remains constant irrespective of the application of a pressing force by the pressing member 21. As an alternative, the fluid inlet device 26 may be configured to make the supply pressure of the fluid variable (f1≠f3) under control by the control unit CP such that the internal pressure of the bag-shaped, film-based vessel 1a changes (increases or decreases) according to the application of a pressing force by the pressing member 21.

If the predetermined time t1 is determined to have elapsed in step 5, the pressing member 21 is retracted via the drive mechanism 25, and the resulting cell culture vessel 1 is then taken out to end the forming, as depicted in FIG. 4D and indicated in step 6 of FIG. 5. On the cell culture vessel 1 so taken out, the above-mentioned depressions 4 and bulge shape have been formed, so that the cell culture vessel 1 of this embodiment has now been manufactured.

Second Embodiment

A second embodiment of the present invention will next be described with reference to FIGS. 6 to 8.

A manufacturing apparatus 30 for the cell culture vessel in the second embodiment is different from the manufacturing apparatus 20 in the first embodiment, for example, in that the vessel support member 23 includes a suction channel 23b, a suction device 27 is included, and temperature control devices 28 are also included.

Therefore, these differences from the first embodiment will hereinafter be described primarily, and components with the same configurations or functions as in the first embodiment will be identified by the same signs as in the first embodiment, and their description will be omitted as desired (this will equally apply to other embodiments and modifications to be described later).

The manufacturing apparatus 30 will be described as a configuration including both the suction device 27 and the temperature control devices 28 in this embodiment, but the manufacturing apparatus 30 is not limited to such a configuration and is required to include at least one of them.

Figure 6:
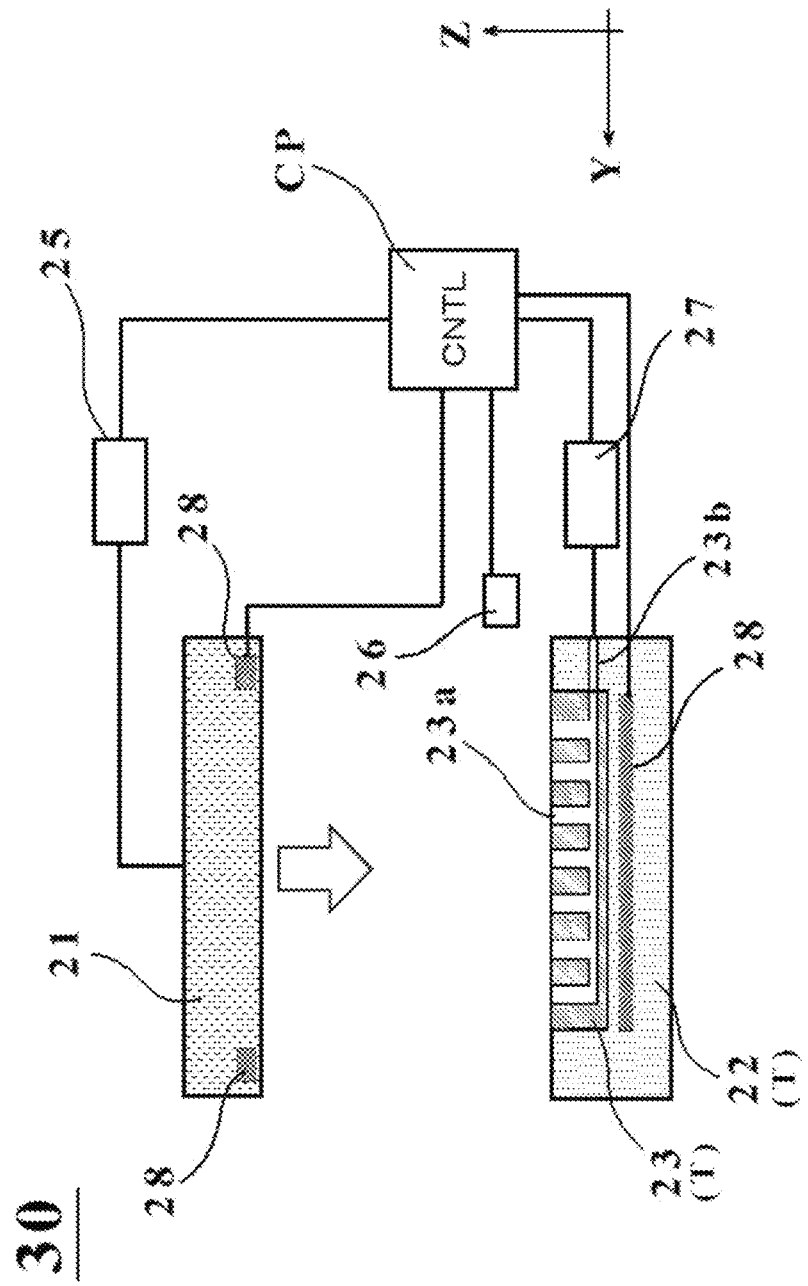
FIG. 6 is a schematic diagram depicting an outline configuration of a manufacturing apparatus 30 for a cell culture vessel according to a second embodiment.

As depicted in FIG. 6, the manufacturing apparatus 30 for the cell culture vessel is configured by further including the suction device 27 and having the temperature control devices 28 as substitutes for the heating devices 24.

The suction device 27 has a function to suction a bag-shaped, film-based vessel 1a which is placed on the placement stage T, through the plurality of concave portions 23a formed on the placement stage T when fluid has been introduced into the bag-shaped, film-based vessel 1a. The vessel support member 23 in this embodiment includes the suction channel 23b in communication with the concave portions 23a, and this suction channel 23b extends through a part of the placement stage main member 22 and is connected to the suction device 27.

The suction device 27 is connected to an undepicted negative pressure source, and is configured to enable a suction operation through the suction channel 23b under control of the control unit CP. As a consequence, the inside of each concave portion 23a is brought into a negative pressure state when the bag-shaped, film-based vessel 1a is placed, so that the bag-shaped, film-based vessel 1a is sucked at the bottom wall thereof (in other words, the wall placed on the vessel support member 23).

According to the suction device 27 in this embodiment, it is, hence, possible to perform an assist when the above-descried depressions 4 (see FIGS. 1B and 1C) are formed in the bottom wall of the bag-shaped, film-based vessel 1a.

The temperature control devices 28 additionally have a function as a cooling device for cooling at least one of the placement stage T and the pressing member 21 in addition to the function of the heating devices 24 described in the first embodiment. As specific examples of the temperature control devices 28, Peltier devices and the like can be exemplified although a variety of other known devices can also be applied. As each temperature control device 28, a single device having both a heating function and a cooling function may be applied. As an alternative, each temperature control device 28 may have a configuration that includes a heating device, such as a Nichrome wire, and a cooling device, such as a fan, as discrete devices.

[Manufacturing Method of Cell Culture Vessel 1]

Next, with reference to FIGS. 7A through 7E and FIG. 8, a description will be made about a manufacturing method for the cell culture vessel in the second embodiment. FIGS. 7A through 7E are state transition diagrams of the manufacturing apparatus 30 for the cell culture vessel in this embodiment. FIG. 8 is a flow chart illustrating the manufacturing method for the cell culture vessel, the manufacturing method also corresponding to the state transition diagrams of FIGS. 7A through 7E.

Figure 7A:
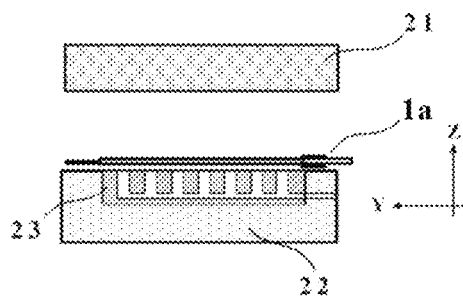
FIGS. 7A through 7E are state transition diagrams of the manufacturing apparatus 30 for the cell culture vessel in the second embodiment.
Figure 8:
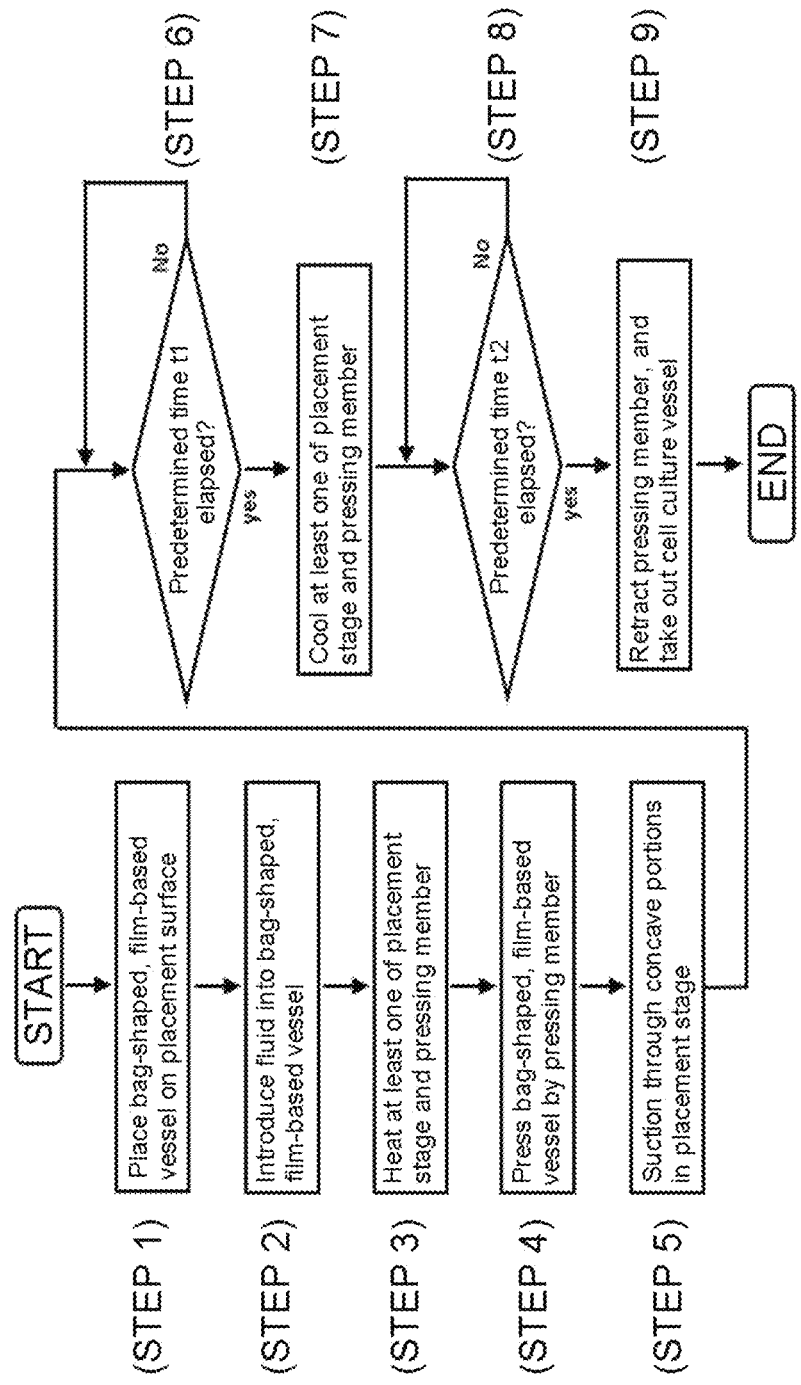
FIG. 8 is a flow chart illustrating a manufacturing method for the cell culture vessel in the second embodiment.

As illustrated in FIG. 7A and indicated in step 1 of FIG. 8, a bag-shaped, film-based vessel 1a is first placed on the placement stage T with the plurality of concave portions 23a formed thereon. At this time, the bag-shaped, film-based vessel 1a may preferably be placed such that its peripheral edge portion is supported on the placement stage main member 22.

Figure 7B:
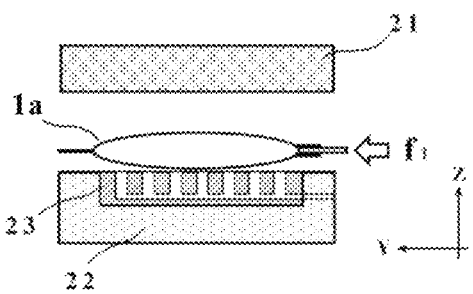

After the bag-shaped, film-based vessel 1a has been placed in step 1, fluid is introduced into the bag-shaped, film-based vessel 1a as illustrated in FIG. 7B and indicated in step 2 of FIG. 8. At this time, the fluid inlet device 26 supplies clean air at a supply pressure f1.

Figure 7C:
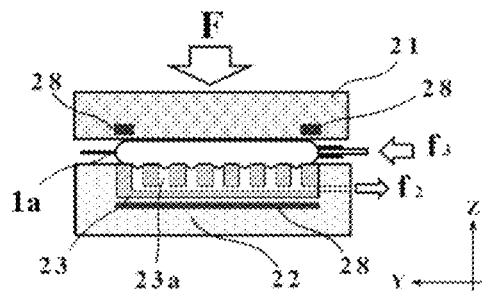

Next, as illustrated in FIG. 7C and indicated in steps 3 to 5 of FIG. 8, at least one of the placement stage T and the pressing member 21 is heated, and the bag-shaped, film-based vessel 1a is pressed by the pressing member 21 and is then suctioned through the concave portions 23a on the placement stage T.

At this time, the heating temperature by the temperature control devices 28 (heating devices) may preferably be set at such a level as making the bag-shaped, film-based vessel 1a soft without melting, for example, at substantially 80° C.

The pressing member 21 is pressing the bag-shaped, film-based vessel 1a under a pressing force F, while the suction device 27 is suctioning the bag-shaped, film-based vessel 1a at a suction force f2. In other words, in this embodiment, a suction operation is performed through the plurality of concave portions 23a formed on the placement stage T when the fluid has been introduced into the bag-shaped, film-based vessel 1a placed on the placement stage T.

The pressing force F and suction force f2 are applied to the bag-shaped, film-based vessel 1a by the pressing member 21 and suction device 27, respectively, as described above. Here, the control unit CP performs control to adjust the supply pressure by the fluid inlet device 26 such that the internal pressure of the bag-shaped, film-based vessel 1a rises a little (in this case, the relationship of f1<f3 is established). As a consequence, it is also possible to suppress an excessive pressure from being applied to the inside of the bag-shaped, film-based vessel 1a. As in the first embodiment, the control unit CP may perform control such that the supply pressure by the fluid inlet device 26 remains at a constant value (in other words, f1=f3) or decreases.

Further, steps 3 to 5 are not necessarily required to be performed in this order, and these steps may be performed concurrently or in a desired different order insofar as they are allowed to proceed in parallel to one another at least in a period of time.

Subsequent to the initiation of step 3 to step 5, a determination is made as to whether or not a predetermined time t1 has elapsed as indicated in step 6 of FIG. 8.

This predetermined time t1 is not particularly limited insofar as the above-described depressions 4 and bulge shape are formed, and may be, for example, substantially several seconds to several minutes.

Figure 7D:
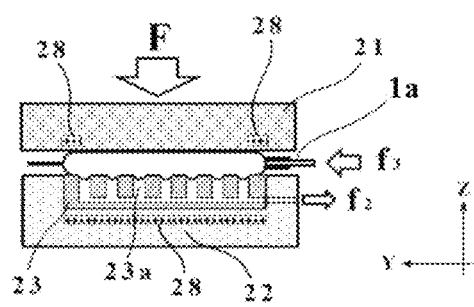

If the predetermined time t1 is determined to have elapsed in step 6, at least one of the placement stage T and the pressing member 21 is cooled as depicted in FIG. 7D and indicated in step 7 of FIG. 8. More specifically, at least one of the temperature control devices 28 functions as a cooling device, and a cooling operation is performed to the region heated by the heating device described above. The cooling temperature by each temperature control device 28 is not particularly limited, and may desirably be of such a level as allowing the film, which has become soft during the forming, to solidify. As this cooling temperature, it is exemplified to cool the bag-shaped, film-based vessel 1a to, for example, substantially 50° C. if the heating has been performed to substantially 80° C.

While at least one of the temperature control devices 28 is performing the above-described cooling operation, the pressing operation by the pressing member 21, the introduction operation of the fluid by the fluid inlet device 26, and the suction operation by the suction device 27 are performed in parallel.

As a consequence, the bag-shaped, film-based vessel 1a is cooled and solidified with its region, which will become the depressions 4 and bulge shape (see FIGS. 1B and 1C) subsequently, being maintained as formed. According to this embodiment, it is, therefore, possible to avoid deformations of the vessel shape upon conducting parting subsequent to the completion of the forming, and to further ensure the formation of the depressions 4 and bulge shape on the cell culture vessel 1.

Subsequent to the initiation of step 7, a determination is made, as indicated in step 8 of FIG. 8, as to whether or not a predetermined time t2 has elapsed.

This determination in step 8 is made based on whether or not the temperature of the bag-shaped, film-based vessel 1a has reached a solidification temperature. Therefore, the predetermined time t2 can be set, for example, at a time calculated by adding a little margin to a time until the above-described solidification temperature is reached. The predetermined time t2 is not particularly limited insofar as the above-described depressions 4 and bulge shape are formed, and may be, for example, substantially several seconds to several minutes.

Figure 7E:
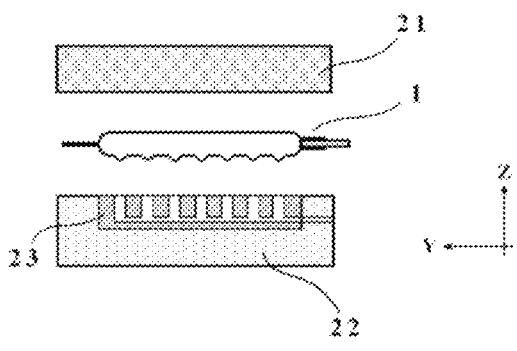

If the predetermined time t2 is determined to have elapsed in step 8, the pressing member 21 is retracted via the drive mechanism 25, and the resulting cell culture vessel 1 is then taken out to end the forming, as depicted in FIG. 7E and indicated in step 9 of FIG. 8. On the cell culture vessel 1 so taken out, the above-mentioned depressions 4 and bulge shape have been formed, so that the cell culture vessel 1 of this embodiment has now been manufactured.

Third Embodiment

A third embodiment of the present invention will next be described with reference to FIG. 9.

A manufacturing apparatus 40 for the cell culture vessel in the third embodiment is different from the manufacturing apparatus 20 in the first embodiment, for example, in that the placement stage main member 22 on which the vessel support member 23 is not mounted serves as a placement stage T and through-holes 22a are formed as substitutes for the concave portions 23a in the placement stage T. In this embodiment, the through-holes are not necessarily required and desired holes other than the through-holes may be formed in the placement stage T.

Figure 9:
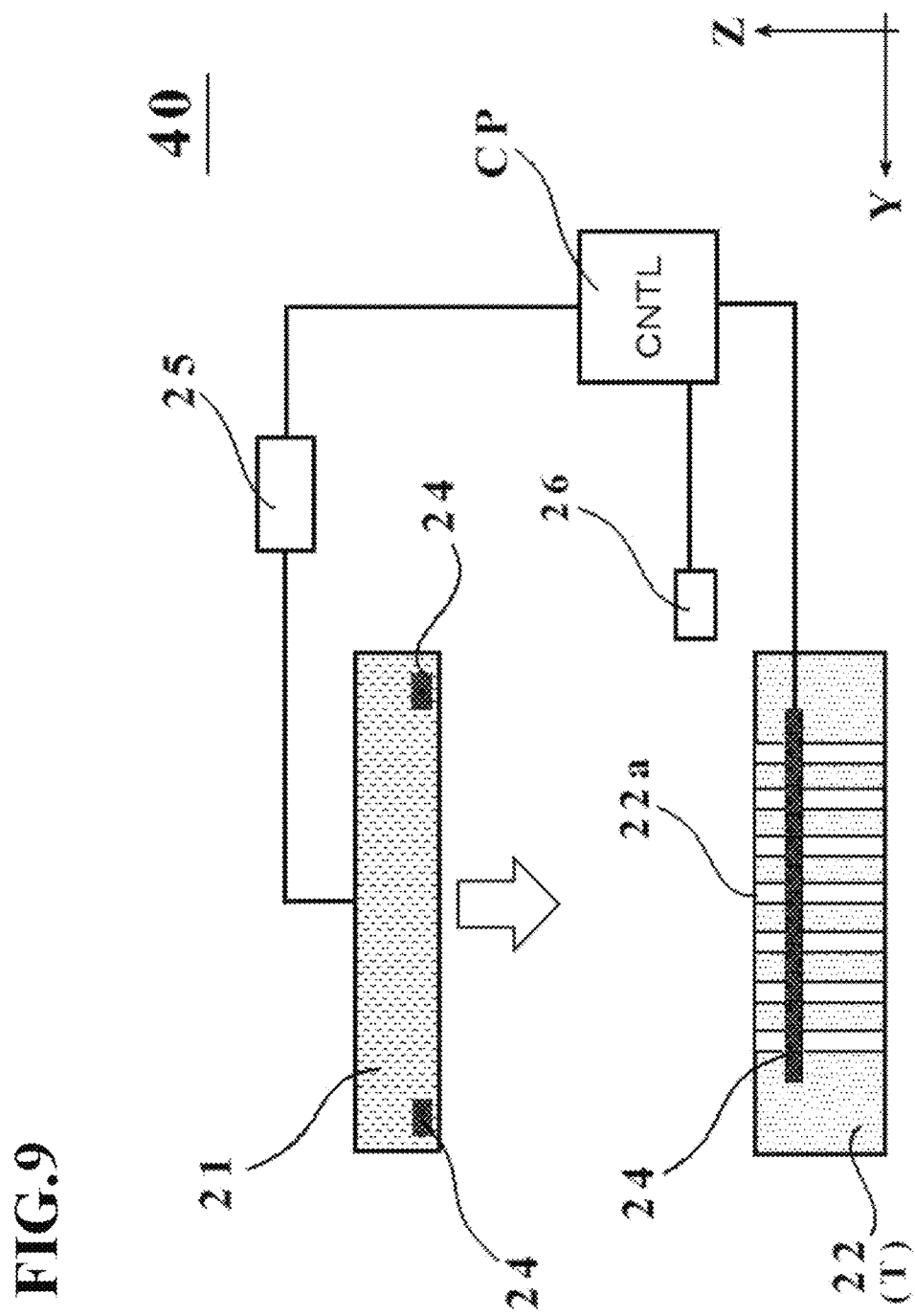
FIG. 9 is a schematic diagram depicting an outline configuration of a manufacturing apparatus 40 for a cell culture vessel in a third embodiment.

In other words, the manufacturing apparatus 40 for the cell culture vessel as depicted in FIG. 9 is configured including the placement stage main member 22 with the through-holes 22a formed therein. The through-holes 22a correspond to the concave portions 23a in the first embodiment, and have a shape extending through the placement stage main member 22 from the placement surface (the surface on which the bag-shaped, film-based vessel 1a is to be placed) to the bottom surface on the opposite side. As appreciated from the above, the concave portions formed on the placement surface, on which the bag-shaped, film-based vessel 1a is to be placed, are not limited to the shape that they do not downwardly penetrate through the placement stage main member 22, but may exist as through-holes as in this embodiment.

Fourth Embodiment

A fourth embodiment of the present invention will next be described with reference to FIGS. 10 through 13.

A manufacturing apparatus 50 for a cell culture vessel in the fourth embodiment is different from the manufacturing apparatus 20 in the first embodiment, for example, in that the manufacturing apparatus 50 includes restraint members 29 and fluid is introduced into a bag-shaped, film-based vessel 1a by the fluid inlet device 26 while restraining the bag-shaped, film-based vessel 1a at peripheral edge portions thereof by the restraint members 29.

The cell culture vessel 1 in the fourth embodiment is also characterized in that the bottom wall with the depressions 4 (see FIGS. 1B and 1C) formed therein is flat and the top wall has an upwardly protruding bulge shape. The term "flat" in this embodiment means a plane in the X-direction and the Y-direction, that is, a single surface which is parallel to the X-Y plane.

Figure 10:
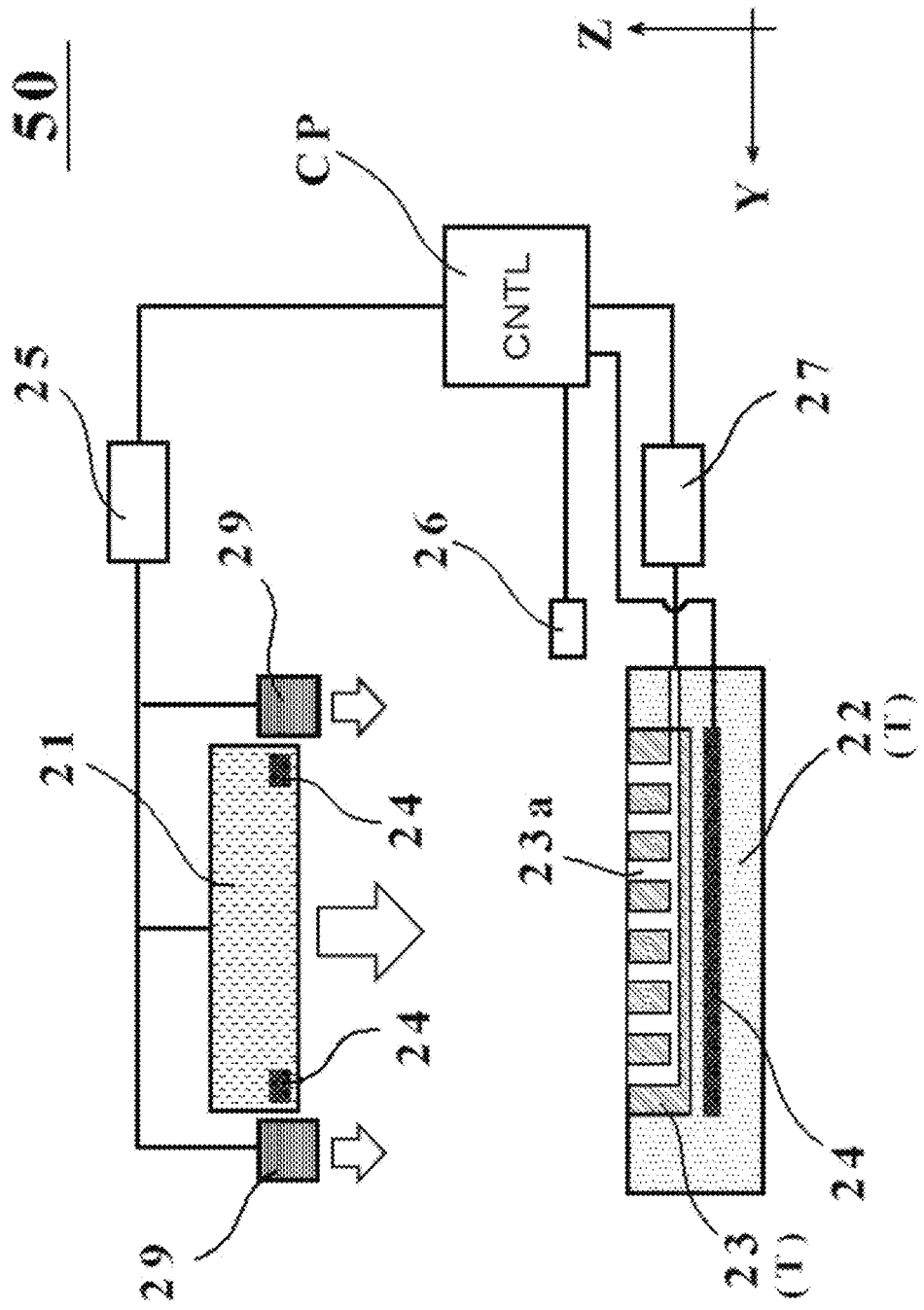
FIG. 10 is a schematic diagram depicting an outline configuration of a manufacturing apparatus 50 for a cell culture vessel in a fourth embodiment.

More specifically, as depicted in FIG. 10, the manufacturing apparatus 50 for the cell culture vessel in this embodiment is configured including the restraint members 29 that restrain the bag-shaped, film-based vessel 1a at the peripheral edge portions thereof. The restraint members 29 are arranged opposite the placement surface, and have a function to restrain the bag-shaped, film-based vessel 1a which is placed on the placement surface, at the peripheral edge portions thereof. Further, the restraint members 29 are configured such that they are allowed to descend independently of the pressing member 21 toward the placement stage T by the drive mechanism 25.

The restraint members 29 and the pressing member 21 are not necessarily required to descend independent of each other. For example, the restraint members 29 may be connected to the drive mechanism 25 via springs to descend together with the pressing member 21.

Further, recessed portions may be formed in the placement stage main member 22 at regions where the placement stage main member 22 opposes the restraint members 29, and a heat-insulating material such as rock wool or urethane resin may be arranged in the recessed portions.

Figure 11:
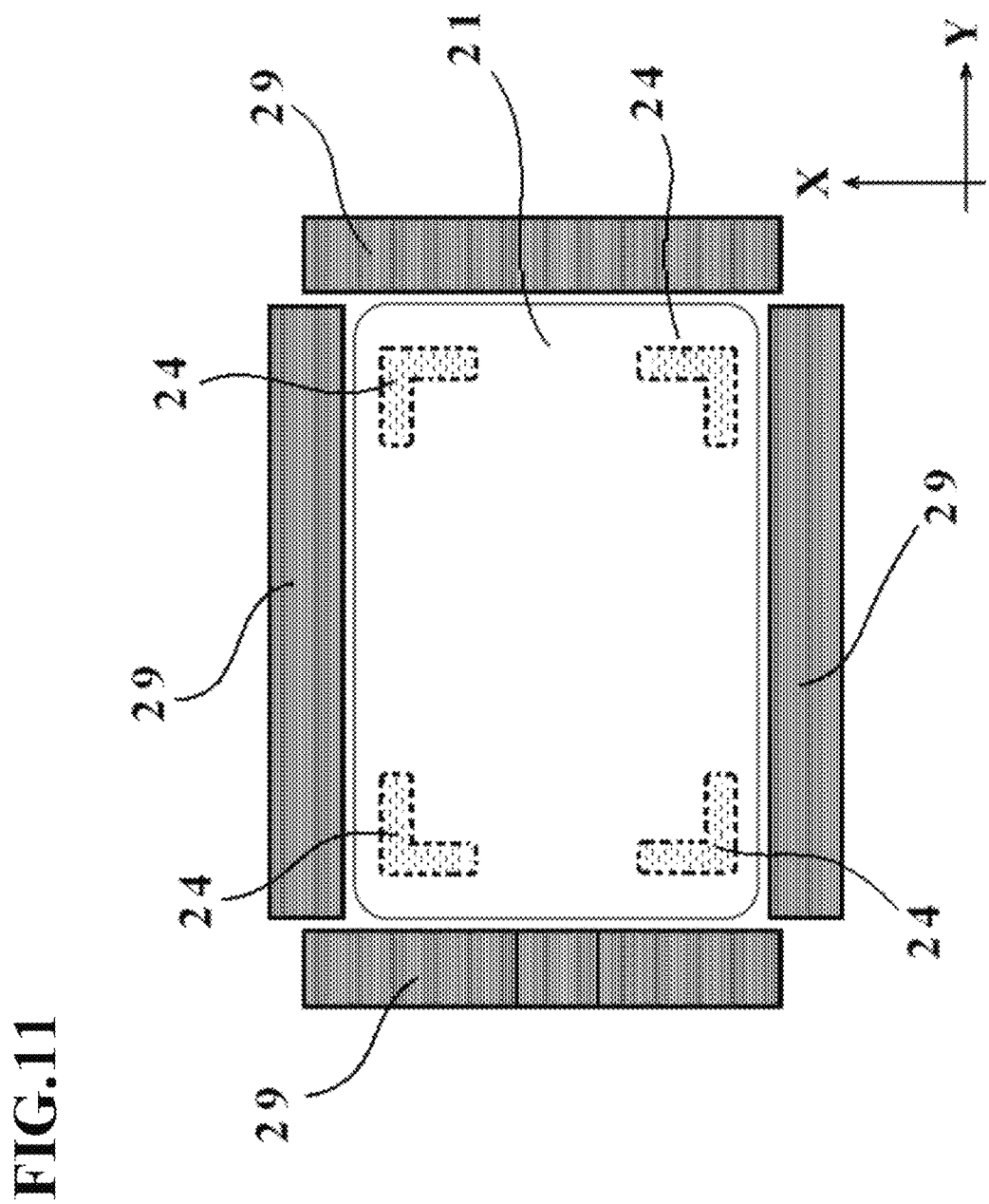
FIG. 11 is a schematic diagram illustrating a positional relationship between a pressing member 21 and restraint members 29 in the manufacturing apparatus 50 for the cell culture vessel in the fourth embodiment.

As illustrated in FIG. 11, the restraint members 29 in this embodiment are disposed around the pressing member 21 such that they oppose the peripheral edge portion of the bag-shaped, film-based vessel 1a. The restraint members 29 are arranged as four separate restraint members in this embodiment, and one of them (the left-side restraint member in FIG. 11) has a shape conforming to the external shape of the charge/discharge port 3. As a consequence, each of the separate restraint members 29 is configured to be able to restrain the bag-shaped, film-based vessel 1a at the peripheral edge portion thereof.

No limitation is imposed on the material of the restraint members 29, and a metal material such as aluminum or iron can be exemplified, for example. Desirably, however, the restraint members 29 may be formed from a material having a lower thermal conductivity than the pressing member 21 such that conduction of heat from the pressing member 21 is reduced as much as possible. The restraint members 29 are not necessarily required to be arranged as four separate restraint members, and may be connected, for example, into an integral structure along the entire periphery as will be described later with reference to FIG. 15 or into a structure that some of the four separate restraint members are connected together.

[Manufacturing Method for Cell Culture Vessel 1]

Next, with reference to FIGS. 12A through 12E and FIG. 13, a description will be made about a manufacturing method for the cell culture vessel in the fourth embodiment. FIGS. 12A through 12E are state transition diagrams of the manufacturing apparatus 50 for the cell culture vessel in this embodiment. FIG. 13 is a flow chart illustrating the manufacturing method for the cell culture vessel, the manufacturing method also corresponding to the state transition diagrams of FIGS. 12A through 12E.

Figure 12A:
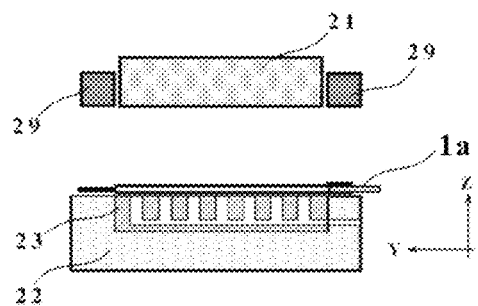
FIGS. 12A through 12E are state transition diagrams of the manufacturing apparatus 50 for the cell culture vessel in the fourth embodiment.
Figure 13:
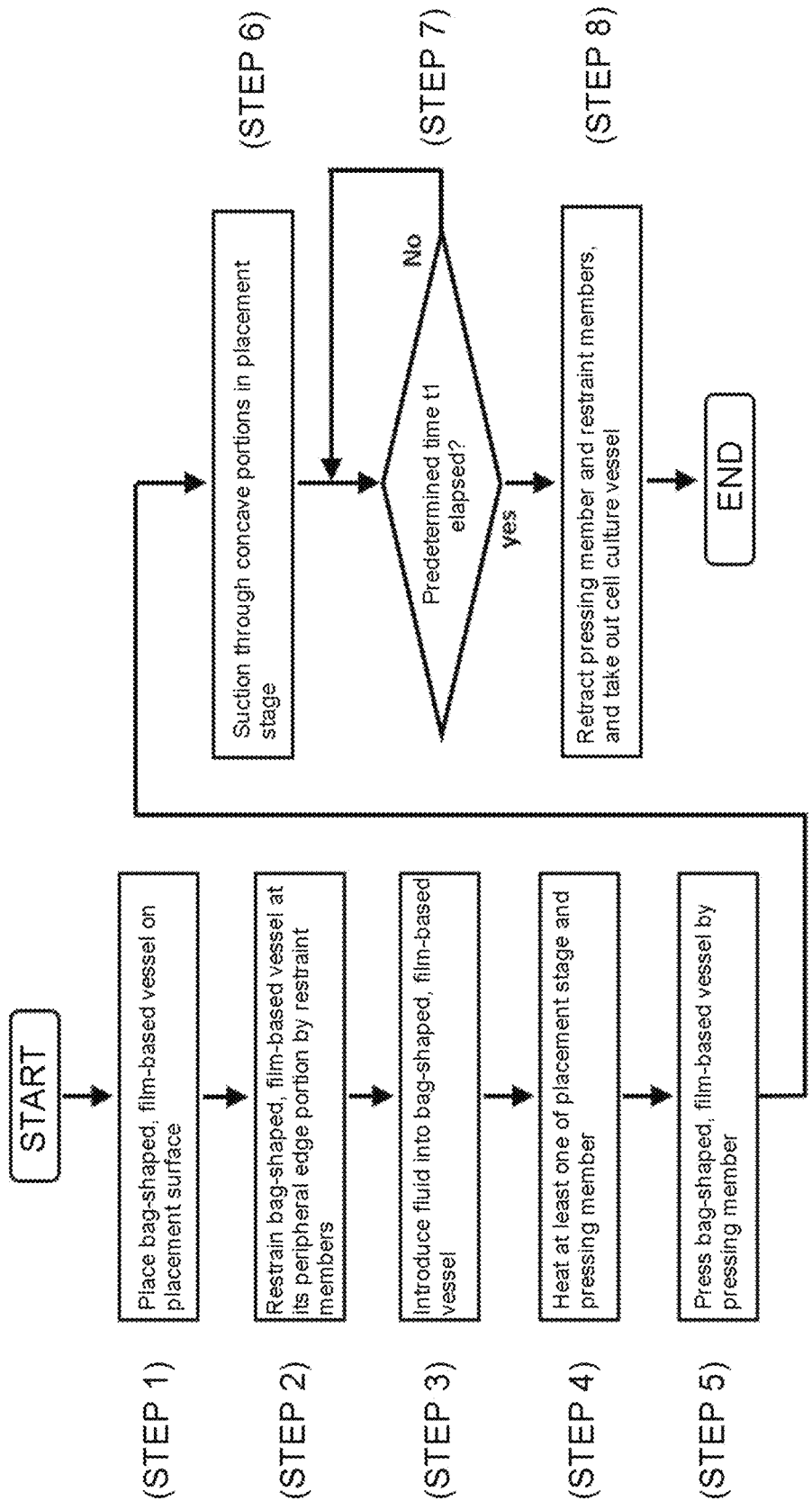
FIG. 13 is a flow chart illustrating a manufacturing method for the cell culture vessel in the fourth embodiment.

As illustrated in FIG. 12A and indicated in step 1 of FIG. 13, a bag-shaped, film-based vessel 1a is first placed on the placement stage T with the plurality of concave portions 23a formed thereon. At this time, the bag-shaped, film-based vessel 1a may preferably be placed such that its peripheral edge portion is supported on the placement stage main member 22.

Figure 12B:
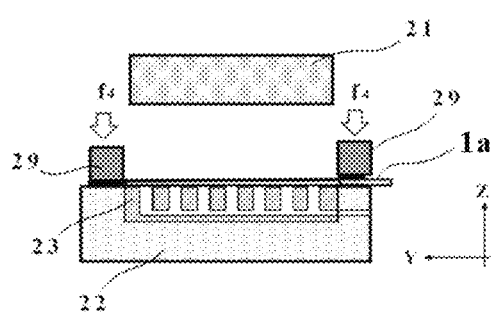

After the bag-shaped, film-based vessel 1a has been placed in step 1, the restraint members 29 descend toward the placement stage T to restrain the bag-shaped, film-based vessel 1a at the peripheral edge portion thereof under a pressing force f4 as illustrated in FIG. 12B and indicated in step 2 of FIG. 13.

Figure 12C:
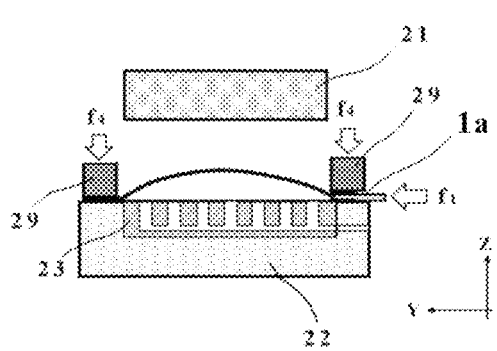

As illustrated in FIG. 12C and indicated in step 3 of FIG. 13, fluid is introduced into the bag-shaped, film-based vessel 1a by the fluid inlet device 26. At this time, the fluid is introduced into the bag-shaped, film-based vessel 1a placed on the placement stage T while restraining the bag-shaped, film-based vessel 1a at the peripheral edge portion thereof by the restraint members 29. In this embodiment, the fluid inlet device 26 also supplies clean air at the supply pressure f1.

Figure 12D:
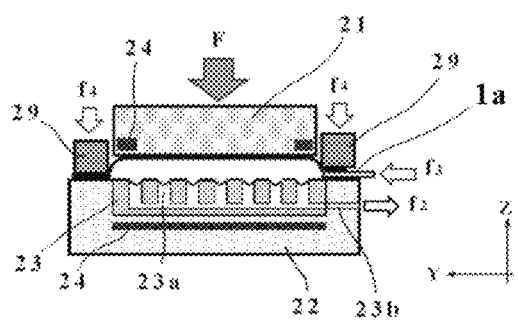

Next, as illustrated in FIG. 12D and indicated in steps 4 to 6 of FIG. 13, at least one of the placement stage T and the pressing member 21 is heated, the bag-shaped, film-based vessel 1a is pressed by the pressing member 21, and further, the bag-shaped, film-based vessel 1a is suctioned through the concave portions 23a of the placement stage T.

At this time, the heating temperature by the corresponding heating device 24 may preferably be set at such a level as making the bag-shaped, film-based vessel 1a soft without melting, for example, at substantially 80° C.

Further, the pressing member 21 is pressing the bag-shaped, film-based vessel 1a under the pressing force F, and the suction device 27 is performing suction under the suction force f2.

The pressing force F and suction force f2 are applied to the bag-shaped, film-based vessel 1a by the pressing member 21 and the suction device 27, respectively, as described above. Here, the control unit CP performs control to change the supply pressure by the fluid inlet device 26 from f1 to f3 such that the internal pressure of the bag-shaped, film-based vessel 1a decreases a little (in this case, the relationship of f1>f3 is established). As a consequence, it is also possible to suppress an excessive pressure from being applied to the inside of the bag-shaped, film-based vessel 1a. The control unit CP may control the supply pressure by the fluid inlet device 26 such that the internal pressure of the bag-shaped, film-based vessel 1a remains constant (in other words, f1=f3) or rises a little.

Further, step 4 to step 6 are not necessarily required to be performed in this order, and these steps may be performed concurrently or in a desired different order insofar as they are allowed to proceed in parallel to one another at least in a period of time.

Subsequent to the initiation of steps 4 to 6, a determination is made, as indicated in step 7 of FIG. 13, as to whether or not the predetermined time t1 has elapsed.

This predetermined time t1 is not particularly limited insofar as the above-described depressions 4 and bulge shape are formed, and may be, for example, substantially several seconds to several minutes.

Figure 12E:
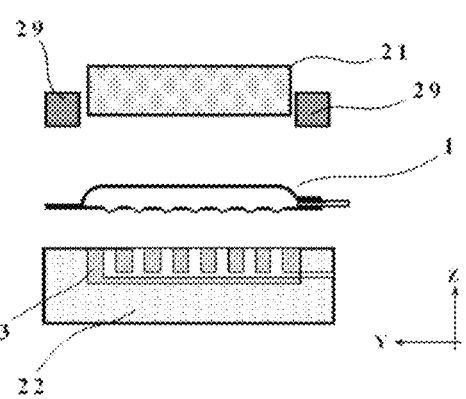

If the predetermined time t1 is determined to have elapsed in step 7, the pressing member 21 is retracted via the drive mechanism 25, and the resulting cell culture vessel 1 is then taken out to end the forming, as depicted in FIG. 12E and indicated in step 8 of FIG. 13. On the cell culture vessel 1 so taken out, the depressions 4 (see FIGS. 1B and 1C) have been formed, and the bulge shape with the upwardly protruding top wall have also been formed, so that the cell culture vessel 1 of this embodiment has now been completed.

To the first embodiment to the fourth embodiment described above, various modifications are feasible within a scope not departing from the spirit of the present invention. A description will hereinafter be made about modifications which can be applied as desired to the first embodiment to the fourth embodiment described above.

Modification 1

Figure 14:
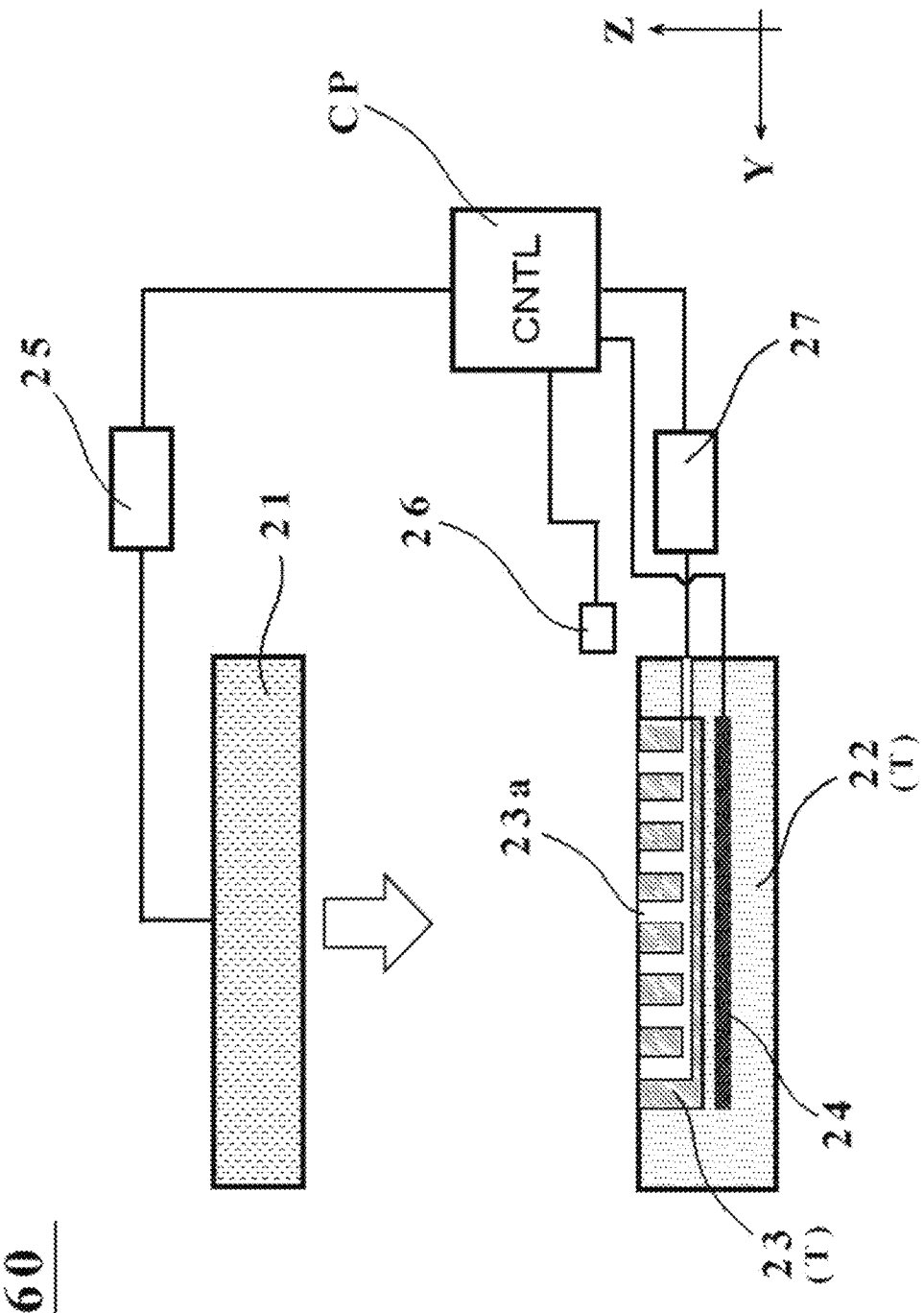
FIG. 14 is a schematic diagram depicting an outline configuration of a manufacturing apparatus 60 for a cell culture vessel in Modification 1.

FIG. 14 is a schematic diagram depicting an outline configuration of a manufacturing apparatus 60 for a cell culture vessel according to Modification 1.

The heating devices 24 or the temperature control devices 28 in each embodiment described above are arranged in each of the pressing member 21 and the placement stage T. However, the present invention is not limited to these configurations, and a single heating device 24 (or temperature control device 28) may be arranged in at least one of the pressing member 21 and the placement stage T.

As depicted specifically in FIG. 14, the manufacturing apparatus 60 for the cell culture vessel has a configuration that the heating device 24 is not embedded in the pressing member 21 but is embedded in the vessel support member 23. Obviously, this Modification 1 may have a configuration that the heating device 24 is not embedded in the vessel support member 23 but is embedded in the pressing member 21.

Modification 2

Figure 15:
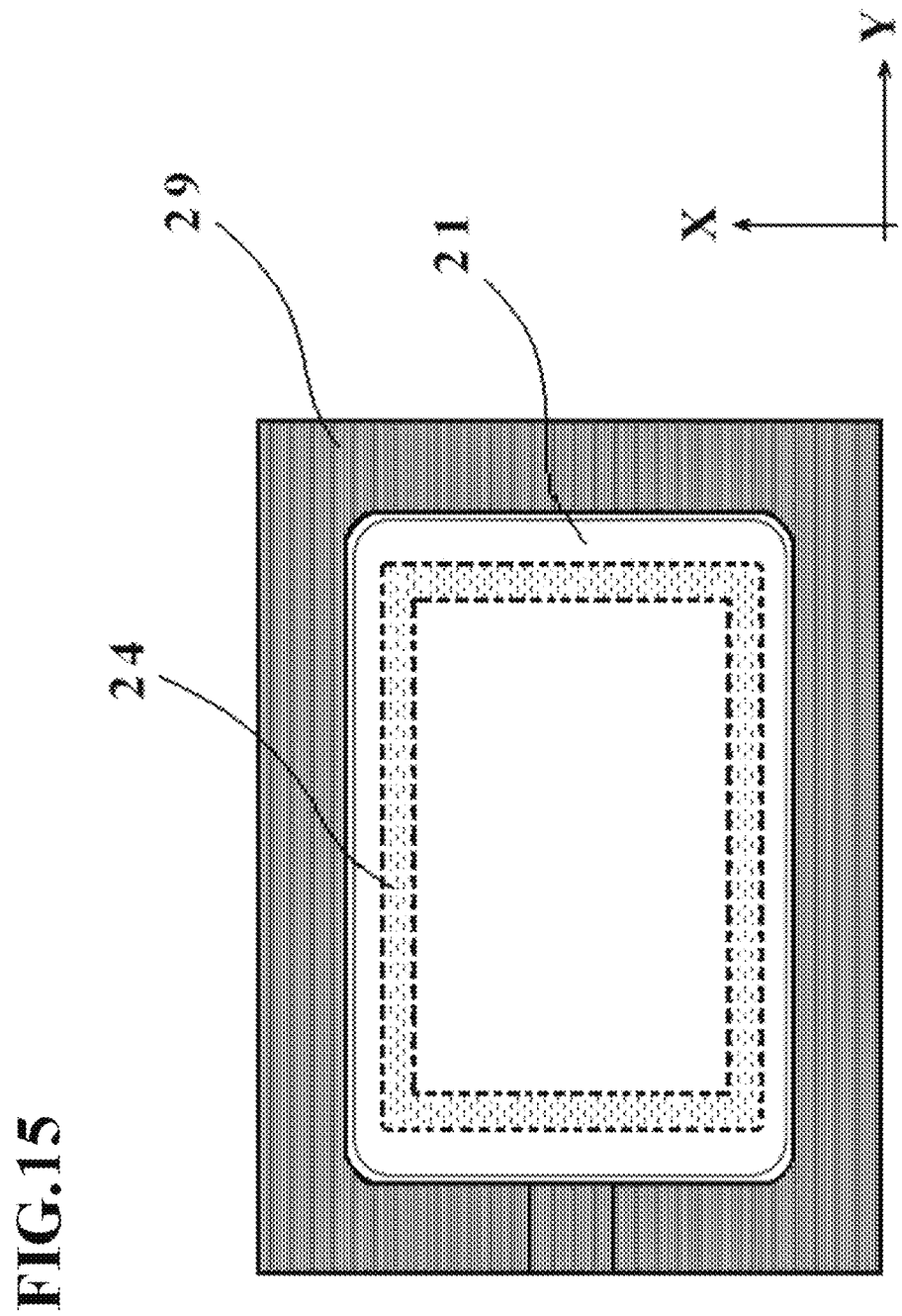
FIG. 15 is a schematic diagram depicting a heating device 24 and a restraint member 29 in Modification 2.

FIG. 15 is a schematic diagram depicting outline configurations of a restraint member 29 and a heating device 24 in Modification 2. In the fourth embodiment described with reference to FIG. 11, the restraint members 29 are configured as the plurality of separate restraint members, and the heating devices 24 embedded in the pressing member 21 are also configured as the plurality of separate heating devices.

However, the present invention is not limited to such configurations, and as depicted in FIG. 15, the restraint member 29 may have such a continuous shape as surrounding the periphery of the pressing member 21.

Also, the heating device 24 embedded in the pressing member 21 may be configured to be in a ring-shaped (annular) form corresponding to positions where the bag-shaped, film-based vessel 1a is formed into a peripheral edge of the top wall 2a of the cell culture vessel 1.

As also depicted in FIG. 15, it is preferred to set as narrow as possible the clearance between the restraint member 29 and the pressing member 21 because, if this clearance is large, the film would be stretched at the position of the clearance when fluid (air or the like) is charged into the bag-shaped, film-based vessel 1a. From the viewpoint of avoiding such a problem, it is desired to bring the outer boundary of an inner opening of the restraint member 29, into which the pressing member 21 can be inserted, as close to the outer edges of the pressing member 21 (in other words, the profile of the bag-shaped, film-based vessel 1a) as possible, and also to form corner portions of the inner opening of the restraint member 29 into a rounded shape like the corner portions of the pressing member 21.

Modification 3

Figure 16:
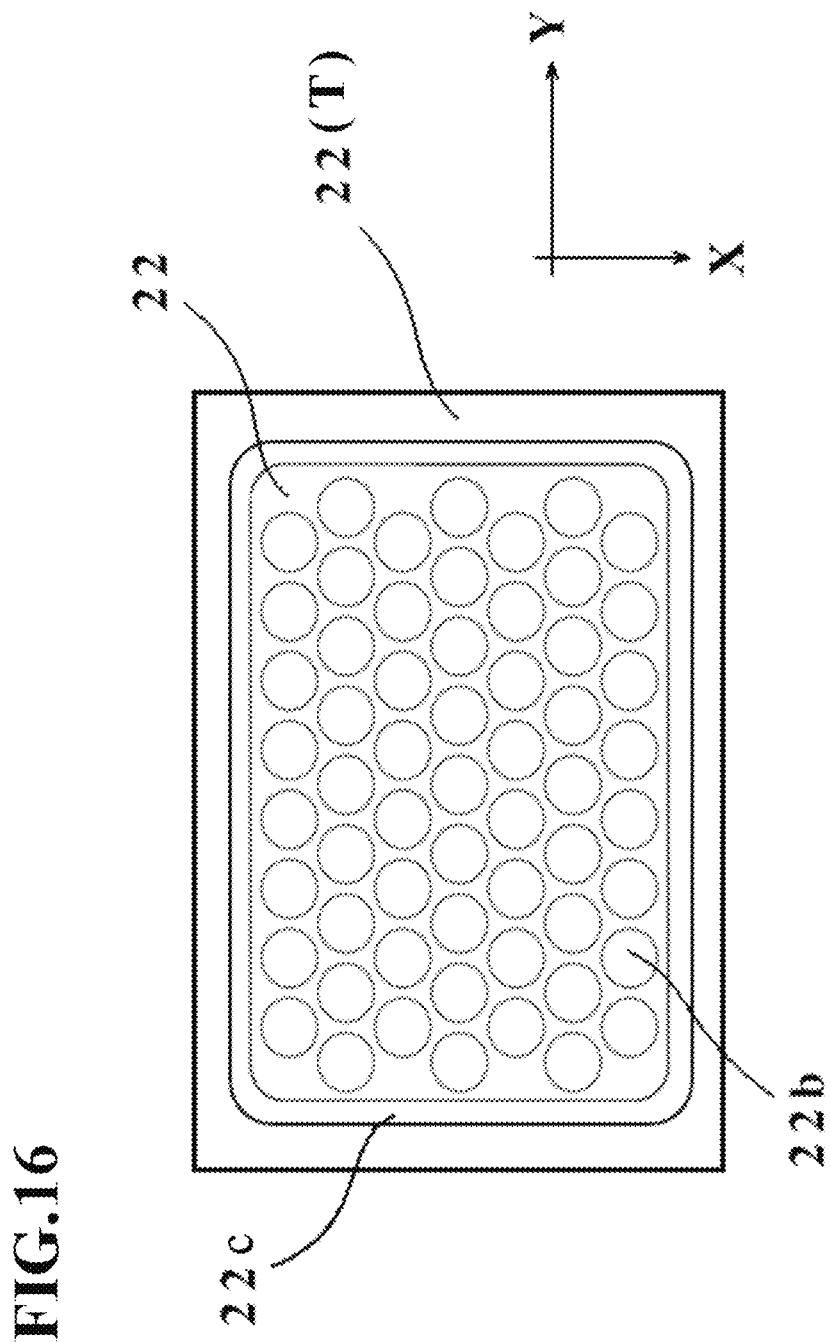
FIG. 16 is a schematic diagram depicting a placement stage T in Modification 3.

FIG. 16 is a schematic diagram depicting an outline configuration of a placement stage T according to Modification 3.

In the first, the second, and the fourth embodiments described above, the placement stage T is configured of the placement stage main member 22 and the vessel support member 23. However, the present invention is not limited to such a configuration. For example, in the upper surface of the placement stage main member 22, concave portions 22b may be formed corresponding to the above-described concave portions 23a, and a heat-insulating groove 22c may also be formed.

In other words, the placement stage T may be configured of the placement stage main member 22. The width and depth of the heat-insulating groove 22c are not particularly limited, and may be set, for example, substantially at 1 to 5 mm in width and at 5 to 10 mm in depth, respectively.

Upon manufacturing the cell culture vessel 1, the peripheral edge portion of the bag-shaped, film-based vessel 1a may be placed, for example, on a region outer than the heat-insulating groove 22c, and further the remaining section of the bag-shaped, film-based vessel 1a, where the depressions 4 will be formed subsequently, may be placed on a section inside the heat-insulating groove 22c.

Therefore, heat occurred in the section on the side of the concave portions 22b is intercepted by the heat-insulating groove 22c, and is suppressed from reaching the peripheral edge portion of the bag-shaped, film-based vessel 1a.

If it is not necessary to consider too much thermal effects, for example, on the peripheral edge portion of the bag-shaped, film-based vessel 1a, the heat-insulating groove 22c is not essential and may be omitted as desired.

Fifth Embodiment

[Cell Culture Vessel 10]

Figure 17:
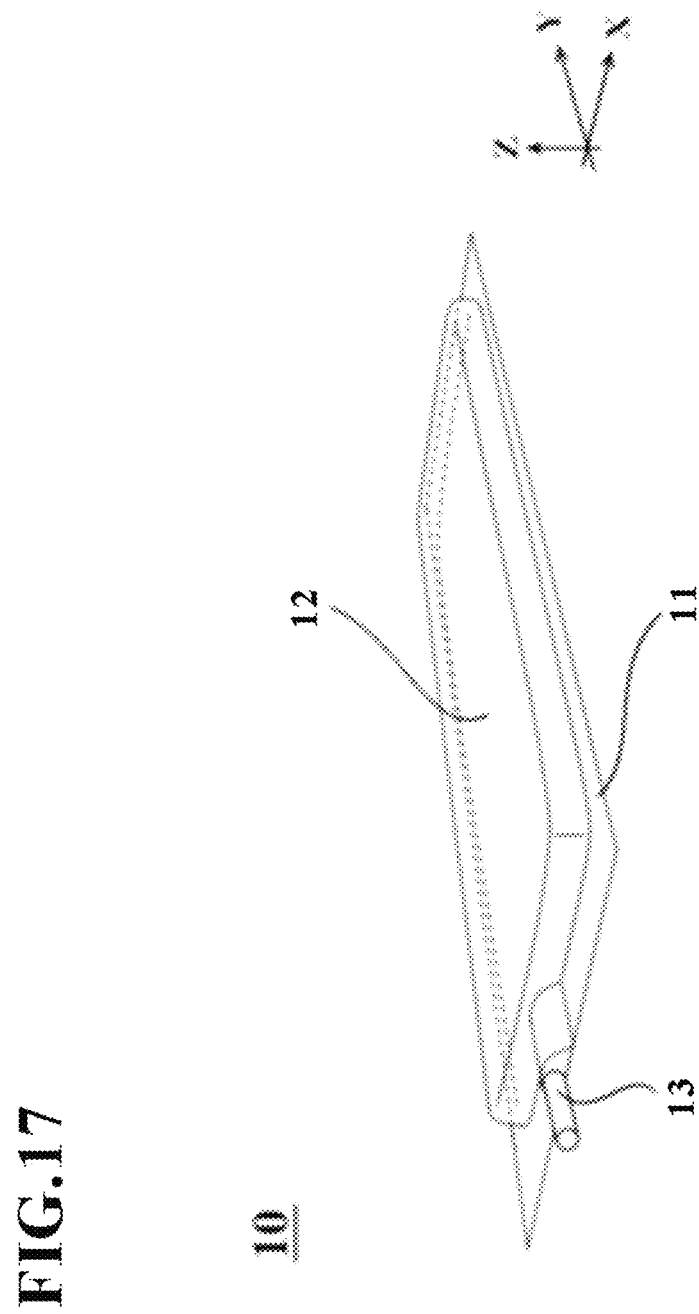
FIG. 17 is an external perspective view of a cell culture vessel 10 according to a fifth embodiment.

FIG. 17 is an external perspective view of a cell culture vessel 10 according to the fifth embodiment of the present invention.

The cell culture vessel 10 is a vessel for culturing cells, which has been formed into a bag shape by using a film-based, soft packing material as a starting material and has flexibility. This cell culture vessel 10 has gas permeability suited for culturing cells, and may preferably have transparency at a part or the entire part thereof such that its contents can be seen.

Figure 18:
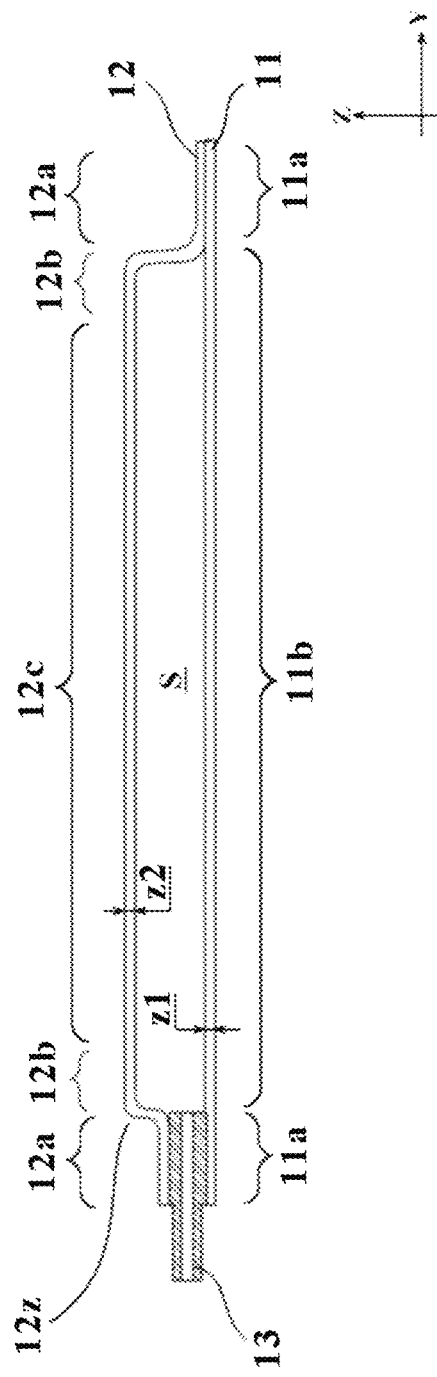
FIG. 18 is a side view of the cell culture vessel 10 according to the fifth embodiment.

As depicted in FIG. 18, the cell culture vessel 10 is configured including at least a first vessel wall 11, a second vessel wall 12, and a charge/discharge port 13. Preferably, the cell culture vessel 10 may have a rectangular external shape that is, for example, of 20 to 1000 mm in the X-direction and 20 to 1000 mm in the Y-direction.

The first vessel wall 11 is formed of a flat film, which has gas permeability and will become a bottom wall. As depicted in FIG. 18, the first vessel wall 11 in this embodiment may preferably have a thickness z1 of 30 to 200 μm, for example. Here, the term "bottom wall" in this embodiment means a wall which, when the cell culture vessel 10 is placed on a placement stage or the like, becomes a bottom and is located on a side lower than the below-described second vessel wall 12 in the Z-direction. Further, the term "flat" in this embodiment means a plane in the X-direction and the Y-direction, that is, a single surface which is parallel to the X-Y plane.

The gas permeability which the first vessel wall 11 has may preferably be 5000 mL/m²·day·atm or more in terms of oxygen permeability as measured at a test temperature of 37° C. in accordance with JIS K 7126 Gas Permeability Testing Method.

In addition, the film which makes up the first vessel wall 11 may preferably have transparency at a part or the entire part thereof such that the status of progress of the culture of cells, the conditions of cells, and the like can be seen. No particular limitation is imposed on a material to be used in such a film insofar as the material has the above-described gas permeability. Illustrative are thermoplastic resins such as polyethylene, polypropylene, ethylene-vinyl acetate copolymer, polyesters, silicone-based elastomers, polystyrene-based elastomers, and tetrafluoroethylene-hexafluoropropylene copolymer (FEP). Such a material may be used as a single layer, or such a material or two or more different ones of such materials may be used as a laminate. Taking into account the thermal fusion bondability upon sealing peripheral edge portion 11a, however, the plastic film may preferably have a layer that functions as a sealant layer.

As also depicted in FIG. 18, the first vessel wall 11 is configured including the peripheral edge portion 11a and a central section 11b. Of these, the peripheral edge portion 11a is a region that opposes a peripheral edge portion 12a of the second vessel wall 12 to be described subsequently herein. The central section 11b is a section on a side inner than the above-described peripheral edge portion 11a, and is a section that forms a culture space S to be described later.

The second vessel wall 12 is in contact with the peripheral edge portion 11a of the first vessel wall 11, and has a bulge shape 12z protruding away from the first vessel wall 11 on a side inner than the peripheral edge portion 11a. Similar to the first vessel wall 11, the second vessel wall 12 is formed of a film having gas permeability.

More specifically, the gas permeability which the second vessel wall 12 has may preferably be 5000 mL/m²·day·atm or more in terms of oxygen permeability as measured at a test temperature of 37° C. in accordance with JIS K 7126 Gas Permeability Testing Method. Therefore, the gas permeability of the second vessel wall 12 may be set equal to the gas permeability of the first vessel wall 11. In addition, the film which makes up the second vessel wall 12 may preferably have transparency at a part or the entire part thereof such that the status of progress of the culture of cells, the conditions of cells, and the like can be seen, and may be made from the same material as the first vessel wall 11.

As also depicted in FIG. 18, the second vessel wall 12 in this embodiment may preferably have a thickness z2 of 30 to 200 µm, for example. Therefore, the thickness z2 of the second vessel wall 12 may be set equal to the thickness z1 of the first vessel wall 11. In other words, the thickness ratio of the first vessel wall 11 to the second vessel wall 12 may be set at substantially 1.

The second vessel wall 12 is configured including the peripheral edge portion 12a, a rise portion 12b, and a central section 12c. Of these, the peripheral edge portion 12a is a portion in contact with the peripheral edge portion 11a of the first vessel wall 11. The central section 12c is a section on a side inner than the rise portion 12b to be described subsequently herein, and is a section arranged apart from the central section 11b in the Z-direction by a desired height to form the culture space S. The rise portion 12b is a region rising from the first vessel wall 11 such that the central section 12c is apart from the first vessel wall 11.

In this embodiment, the peripheral edge portion 11a of the first vessel wall 11 and the peripheral edge portion 12a of the second vessel wall 12 may be sealed together by heat welding, whereby the gas tightness of the culture space S is further ensured. However, their sealing is not limited to this manner, and may be conducted in a manner that fixes the peripheral edge portion 11a of the first vessel wall 11 and the peripheral edge portion 12a of the second vessel wall 12 together, for example, via a known adhesive.

Under the concept of ensuring as wide a flat culture surface as possible with culture liquid spreading in uniform thickness dimension, the narrower the width of the rise portion 12b, the better, and the narrower the width of a sealed region at the peripheral edge portion, the better, as well.

In this embodiment, the bulge shape 12z protruding in a plateau shape is formed by the above-mentioned rise portion 12b and central section 12c, and the culture space S is formed inside this bulge shape 12z. The height of the culture space S in the Z-direction is not particularly limited, and may be set as needed such that an appropriate liquid thickness dimension is obtained corresponding to the conditions of cells under culture. The height of the culture space S in the Z-direction may be, for example, several millimeters to several tens millimeters although it also relies upon the size of the culture vessel.

As depicted in FIG. 18 or FIG. 19, the central section 12c may be flat. In other words, the top wall (central section 12c) in the second vessel wall 12, the top wall (central section 12c) forming the culture space S, may preferably be flat. The rise portion 12b of the second vessel wall 12 is a region where the film has deformed by heating into a portion of the plateau shape as will be mentioned later, and may have a higher hardness than the central section 12c. In other words, the hardness of the rise portion 12b that forms the bulge shape 12z in the second vessel wall 12 may be set higher than the hardness of the section (central section 12c) different from the rise portion 12b in the bulge shape 12z. Further, the hardness of the central section 12c may be set equal to the hardness of the central section 11b. In other words, the hardness at the central section 12c in the second vessel wall 12 may be set substantially equal to the hardness at the central section 11b in the first vessel wall 11, the central section 11b opposing the central section 12c.

As depicted in FIGS. 18 and 19, the charge/discharge port 13 is a member communicating to the culture space S surrounded by the first vessel wall 11 and the second vessel wall 12. The charge/discharge port 13 is a tubular member through which culture liquid, cells, and the like can flow. Using, for example, a thermoplastic resin such as polyethylene, polypropylene, polyvinyl chloride, a polystyrene-based elastomer, or FEP, the charge/discharge port 13 can be formed into a predetermined shape by injection molding, extrusion, or the like.

To avoid blocking of the charge/discharge port 13 by sticking between the central section 12c of the second vessel wall 12 and the central section 11b of the first vessel wall 11, the charge/discharge port 13 may include a port blocking preventing strut that extends from a proximal end into the culture space S. If such a port blocking preventing strut is included, the port blocking preventing strut may preferably be disposed such that it is located on the side of the central section 12c in the culture space S to avoid interference with cells existing on the surface of the central section 11b in the first vessel wall 11.

In this embodiment, the charge/discharge port 13 may be configured such that the charge/discharge port 13 has a semicircular cross-sectional shape, has a flat shape at a surface where the charge/discharge port 13 is in contact with the first vessel wall 11, and has a curved shape at a surface where the charge/discharge port 13 is in contact with the second vessel wall 12.

As a consequence, the occurrence of a clearance is suppressed between the charge/discharge port 13 and the second vessel wall 12, and therefore, the culture liquid is prevented from leaking out of the culture space S.

In this embodiment, at least the inner surface of the first vessel wall 11 and the top wall of the second vessel wall 12 may preferably be parallel to each other. As a consequence, the culture space S can be ensured to be large, so that the culture liquid is allowed to flow efficiently to every corner of the culture space S even if the quantity of the culture liquid is relatively small.

More preferably, the inner surface of the first vessel wall 11, the inner surface of the second vessel wall 12 (the top wall, the central section 12c) and the bottom surface of the charge/discharge port 13 may be parallel to one another as depicted in FIG. 19. In other words, the bottom surface of the charge/discharge port 13 (the surface of the charge/discharge port 13, where the charge/discharge port 13 is in contact with the first vessel wall 11) in this embodiment may preferably be in flush with the surface of the first vessel wall 11. As a consequence, a relatively small quantity of culture liquid is allowed to flow more efficiently to every corner of the culture space S.

[Manufacturing Method for Cell Culture Vessel 10 and Manufacturing Apparatus for Cell Culture Vessel 10]

With reference to FIGS. 20A through 20E, a description will next be made about a manufacturing method and manufacturing apparatus for the cell culture vessel 10.

The cell culture vessel 10 is manufactured through the following individual steps by using a manufacturing apparatus for the cell culture vessel, the manufacturing apparatus including the pressing member 21, the restraint members 29, the placement stage T, the heating devices 24, and the fluid inlet device 26 to be described respectively hereinafter.

Figure 20A:
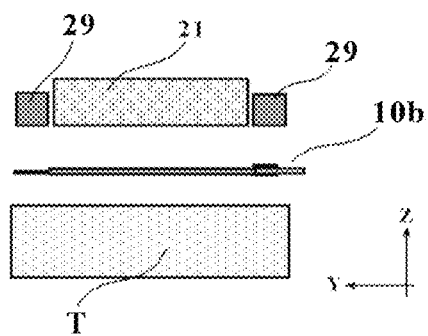
FIGS. 20A through 20E are diagrams illustrating a manufacturing apparatus and method for the cell culture vessel 10 in the fifth embodiment.

As illustrated in FIG. 20A, the first vessel wall 11 which is formed of the film having gas permeability, and the second vessel wall 12 which is disposed opposite the first vessel wall 11, are first placed on the placement stage T in a superimposed state. It is preferred that, at this time, the peripheral edge portion 11a of the first vessel wall 11 and the peripheral edge portion 12a of the second vessel wall 12 be sealed together, for example, by heat welding.

It is also preferred that the above-described charge/discharge port 13 be arranged between an end portion of the first vessel wall 11 and that of the second vessel wall 12. An assembly of the first vessel wall 11, the second vessel wall 12, and the charge/discharge port 13 as illustrated in FIG. 20A will be referred to as a "preform 10b" as a cell culture vessel before completion.

Figure 20B:
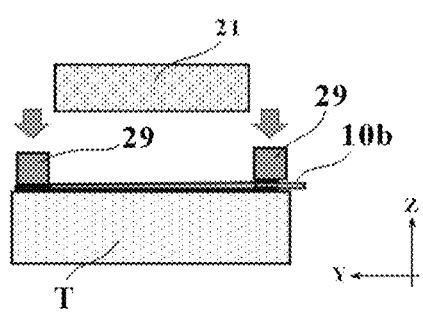

After the first vessel wall 11 has been placed on the placement stage T, the peripheral edge portion 12a of the second vessel wall 12 is pressed and restrained by the restraint members 29 in a state that the second vessel wall 12 is maintained free from being pressed (in an unpressed state) at the central section 12c, as illustrated in FIG. 20B. In this manner, the restraint members 29 are arranged opposite the placement stage T, and have a function to restrain the second vessel wall 12 which is placed on the placement stage T, at the peripheral edge portion 12a thereof.

No particular limitation is imposed on the shape of the restraint members 29 insofar as the above-described peripheral edge portion 12a can be restrained. Preferred is a shape that allows to restrain the peripheral edge portion 12a of the second vessel wall 12 neither excessively nor insufficiently, and desired is a shape that allows to restrain all the four sides of the peripheral edge, which include regions corresponding R portion. In this embodiment, the peripheral edge portion 12a of the second vessel wall 12 is restrained using the restraint members 29. However, the restraint members 29 may be omitted as desired if the flatness of the first vessel wall 11 is ensured.

Figure 20C:
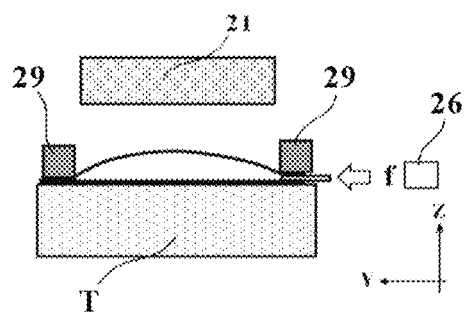

After the peripheral edge portion 12a of the second vessel wall 12 has been restrained by the restraint members 29, fluid is introduced between the first vessel wall 11 and the second vessel wall 12 by using the fluid inlet device 26 in a state that the peripheral edge portion 12a is pressed by the restraint members 29, as illustrated in FIG. 20C. In this embodiment, the fluid is introduced into the preform 10b (the space between the first vessel wall 11 and the second vessel wall 12) through the charge/discharge port 13. Thus, in this embodiment, the fluid is introduced at a supply pressure f by the fluid inlet device 26 into the space between the first vessel wall 11 and the second vessel wall 12 while restraining the second vessel wall 12 by the restraint members 29.

The fluid to be introduced by the fluid inlet device 26 in this embodiment is liquid or gas. As the liquid, pure water or the like is exemplified. As the gas, clean air or an inert gas such as nitrogen is exemplified. Of these, from the viewpoint of handling and processing ease, clean air is applied in this embodiment.

Figure 20D:
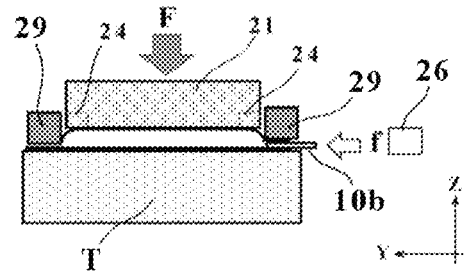

After the fluid has been introduced into the preform 10b, the pressing member 21 is allowed to descend to a position apart by a predetermined distance from the placement stage T as illustrated in FIG. 20D, and at least the pressing member 21 is heated by the heating devices 24 while pressing the central section 12c of the second vessel wall 12 at a pressing force F by the pressing member 21. At this time, the above-described predetermined distance defines the size (height) of the bulge shape 12z of the cell culture vessel 10. Thus, the pressing member 21 is arranged movably up and down relative to the placement stage T, and has a function to press the second vessel wall 12 with the fluid introduced in the space between the first vessel wall 11 and the second vessel wall 12.

As the heating devices 24 in this embodiment, known resistance heating means or the like such as, for example, Nichrome wires may be exemplified. Typically, the heating devices 24 can be arranged inside the pressing member 21. It is also possible to adopt a configuration that the heating devices 24 are arranged inside the placement stage T or a configuration that the heating devices 24 heat at least one of the placement stage T and the pressing member 21.

The temperature at which the heating devices 24 heat the pressing member 21 is determined by taking into consideration the heatproof temperature of the film to be used as the first vessel wall 11 or the like, and heating to such an extent as making the film soft (for example, substantially 80° C.) is preferred. By this heating with the pressing member 21, the above-described bulge shape 12z is formed. When heating is conducted by the pressing member 21, heating means (for example, resistance heating devices such as Nichrome wires) may be arranged in particular regions of the pressing member 21 (regions opposing the peripheral edge portion 12a of the second vessel wall 12 while avoiding a section opposing the central section 12c of the second vessel wall 12). As a consequence, it is possible to suppress such a situation that even regions of the second vessel wall 12, the regions being not necessarily needed for the formation of the bulge shape 12z, may also be hardened.

When pressing the second vessel wall 12 by the pressing member 21 which has been heated to a desired temperature, the supply pressure of the fluid to be introduced into the preform 10b may preferably be controlled by the fluid inlet device 26 such that the internal pressure of the inside (which will become the culture space S subsequently) of the preform 10b remains constant. As a consequence, the application of an excessive pressure to the inside of the preform 10b is suppressed, so that stretching of the film, a failure of the seal, and the like can be avoided.

In addition, a cooling device may also be included in the pressing member 21 or the like to cool the pressing member 21 with the cooling device after heating the pressing member 21 and while pressing the second vessel wall 12.

Figure 20E:
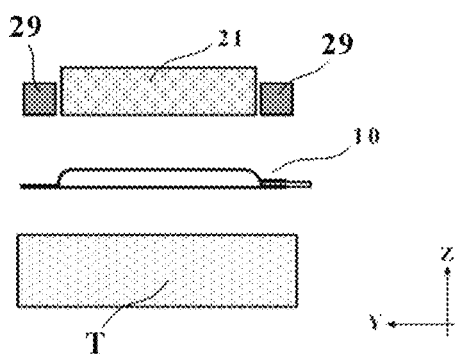

After a predetermined time has elapsed since the initiation of pressing of the second vessel wall 12 by the pressing member 21 heated to the desired temperature, the pressing member 21 and the restraint members 29 are retracted relative to the placement stage T as illustrated in FIG. 20E, and the cell culture vessel 10 so completed is taken out to end the forming. Sealing may preferably be applied to the charge/discharge port 13 of the cell culture vessel 10 before retracting the pressing member 21 and the restraint members 29 relative to the placement stage T. By such sealing, contaminants and the like are suppressed from unexpectedly penetrating into the culture space S.

Significance of Having Flat Inner Bottom Surface and Bulge Shape

Conventional cell culture vessels include, to some extent, those which have a shape that an inner bottom surface as a culture surface for cells is flat at only a part thereof, but have absolutely no concept of ensuring the provision of a culture surface to the maximum extent for cells. As for ensuring uniform spreadability for the culture liquid across a culture space, there has not been any presentation of this problem, to say nothing of suggestion of a configuration to resolve the problem. More specifically, a cell culture vessel manufactured by a conventional method, such as that shown in FIGS. 21C and 21D, does not allow culture liquid to spread evenly in the directions of a plane (X-Y plane), so that the culture liquid does not flow to corner parts of the vessel and cannot provide any good culture space. In addition, the vessel also has warpage in the height direction (the Z-direction), leading to the occurrence of irregularity in the thickness dimension of the culture liquid over the entire culture surface.

Figure 21A:
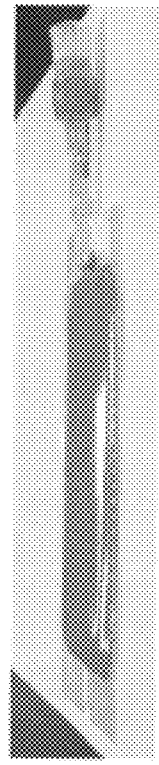
FIGS. 21A through 21D are photos showing a comparison between a cell culture vessel of a conventional type and the cell culture vessel 10 of the fifth embodiment.
Figure 21B:
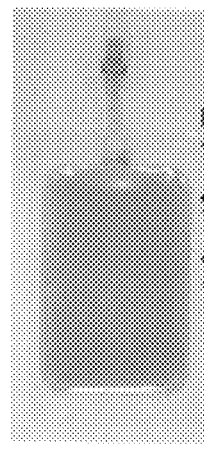
Figure 21C:
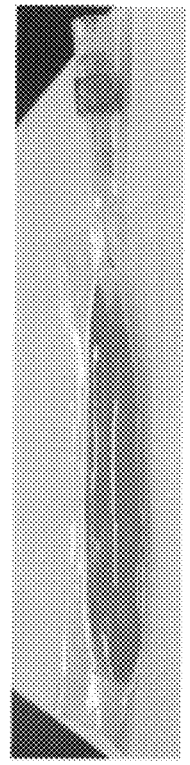
Figure 21D:
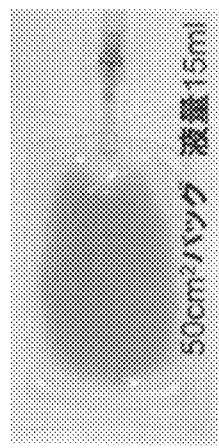

In the cell culture vessel of the fifth embodiment shown in FIGS. 21A and 21B, in contrast, the culture liquid has evidently spread uniformly and evenly in the above-described plane directions and also in the height direction. Thus, the cell culture vessel 10 manufactured in the fifth embodiment allows the culture liquid to evenly flow to every corner over the central section 11b as a culture surface in the first vessel wall 11 even if the culture liquid can be used only in a relatively small quantity. According to the fifth embodiment, it is, therefore, possible to use expensive culture liquid efficiently to the maximum extent, and also to further ensures the culture of precious cells while suppressing a contamination risk.

A cell culture method that uses such a cell culture vessel of the fifth embodiment is a cell culture method that uses the above-described cell culture vessel 10, and is characterized by placing the first vessel wall with the first vessel wall 11 located downward relative to the second vessel wall 12, and charging cells and culture liquid through the charge/discharge port 13. At this time, the cell culture vessel 10 may preferably be placed on a placement surface in a cell culture compartment (e.g., $CO_2$ incubator) controlled at an appropriate temperature (for example, 37° C.), carbon dioxide concentration (for example, 5 to 10% $CO_2$ concentration) and humidity (for example, about 95%).

As a consequence, a flat culture surface can be ensured over a wide range by the first vessel wall as the bottom wall, and culture liquid is allowed to flow to every corner of the culture surface by the second vessel wall having the bulge shape even if the culture liquid is in a small quantity.

In the above-described embodiments, the description is made taking, as an example, adherent cells such as iPS cells, but the present invention is not limited to such an example. More specifically, the present invention may be applied to culture vessels for floating cells such as hematopoietic cells and ascites cells, manufacturing methods and apparatus for the culture vessels, and cell culture methods using the culture vessels, because there is also a practical need to desirably distribute cells evenly over a wide range in static culture of floating cells, and adherent cells also take substantially the same actions as floating cells until they settle on and adhere to the inner bottom wall after seeding.

On the fifth embodiment described above, various modifications are feasible within a scope not departing from the spirit of the present invention. A description will hereinafter be made about some modifications which can be applied to the fifth embodiment.

Modification 4

Figure 22A:
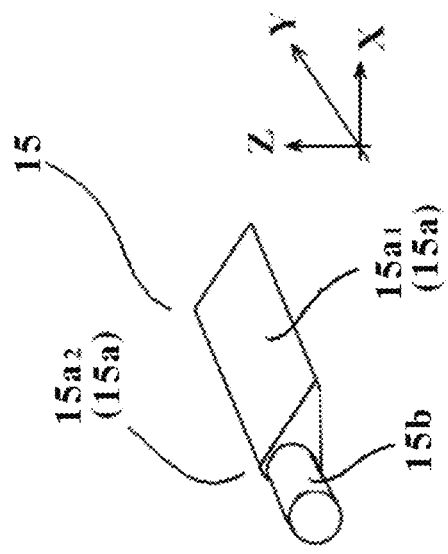
FIGS. 22A and 22B are diagrams depicting two examples of Modification 4 of a charge/discharge port of the cell culture vessel 10 of the fifth embodiment.
Figure 22B:
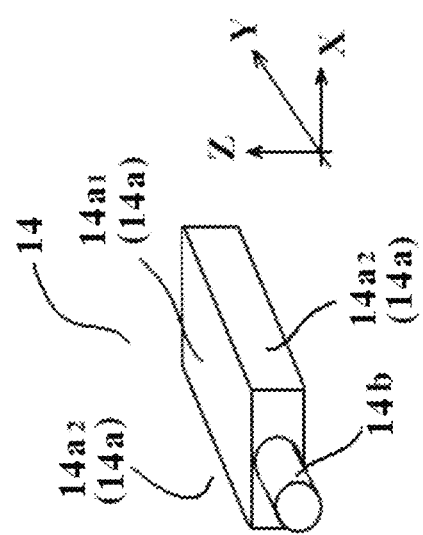

FIGS. 22A and 22B are diagrams depicting modifications of the charge/discharge port 13 described in the fifth embodiment.

The charge/discharge port 13 described in the fifth embodiment has a curved shape at a surface (upper surface) where the charge/discharge port 13 is in contact with the second vessel wall 12. However, the present invention is not limited to such a configuration, and can adopt various port shapes.

Like a charge/discharge port 14 depicted in FIG. 22A, for example, a surface (in this example, an upper surface $14a_1$ and side surfaces $14a_2$) where the charge/discharge port 14 is in contact with the second vessel wall 12 may be flat. In other words, the charge/discharge port 14 may have a structure with a charge/discharge port 14b added to a rectangular parallelepiped main body 14a that extends in the Y-direction.

Like a charge/discharge port 15 depicted in FIG. 22B, for example, a surface (in this example, an inclined surface $15a_1$ and inclined surface $15a_2$) where the charge/discharge port 15 is in contact with the second vessel wall 12 may be flat. In other words, the charge/discharge port 15 may have a structure with a charge/discharge port 15b added to a triangular prismatic main body 15a that extends in the Y-direction.

Modification 5

Figure 23A:
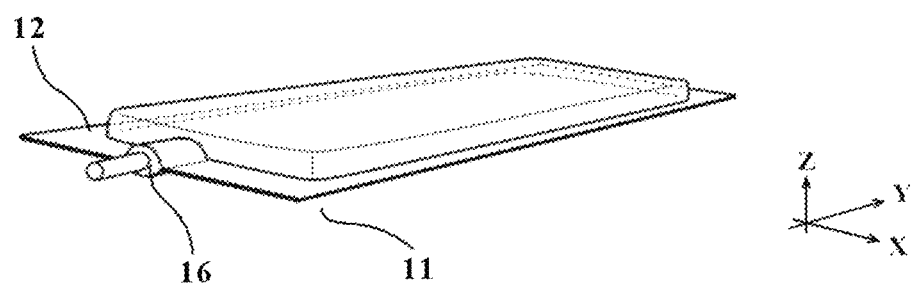
FIGS. 23A to 23C are diagrams depicting a cell culture vessel according to Modification 5.
Figure 23B:
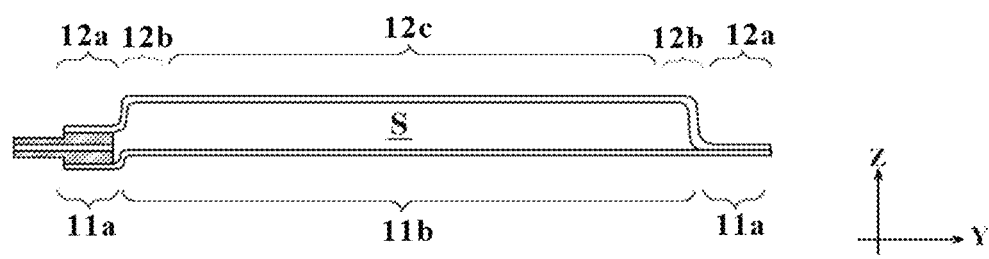
Figure 23C:
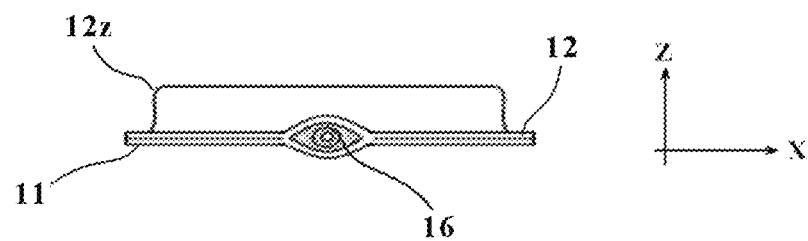

FIGS. 23A to 23C are diagrams depicting a still further modification of the charge/discharge port 13 described in the fifth embodiment.

More specifically, the bottom surfaces of the charge/discharge ports 13, 14, and 15 described above in the fifth embodiment and Modification 4 are each flat, and the outer surface of a region of each first vessel wall 11, where the first vessel wall 11 is in contact with the corresponding charge/discharge port (the peripheral edge portion 11a in contact with the corresponding charge/discharge port), is in flush with the outer surface other than the region that is in contact with the corresponding charge/discharge port.

However, the present invention is not limited to this configuration, and as depicted in FIGS. 23A to 23C, the first vessel wall 11 is required to be flat at least a section thereof other than its region that is in contact with the charge/discharge port 16.

More specifically, a charge/discharge port 16 having a general navicular shape (a cross-sectional shape like an almond) is used in this Modification 5, and the bottom surface of the charge/discharge port 16 is not flat but is a downwardly convex, curved surface. If the charge/discharge port 16 of such a shape is used, a region of the first vessel wall 11, where the first vessel wall 11 is in contact with the charge/discharge port 16, has a downwardly convex, curved surface along the shape of the charge/discharge port 16 as depicted in FIGS. 23A to 23C.

In such a case, the first vessel wall 11 is flat at the section other than the region where the first vessel wall 11 is in contact with the charge/discharge port 16, and therefore, Modification 5 can exhibit the above-described advantageous effects of the present invention.

The vessels of the present invention have been described above with utility directed to the culture of cells, but may also be used for applications other than the culture of cells, for example, when desired to store liquid or the like on an as flat a surface as possible as a bottom surface.

The charge/discharge ports 14 to 16 described above in Modification 4 and Modification 5 may also be applied to the above-described first embodiment to fourth embodiment and Modification 1 to Modification 3 as desired.

Other Modifications

In the first embodiment to the fourth embodiment and Modification 1 to Modification 3 described above, the description is made of the examples in each of which the array of the concave portions 23a (or through-holes 22a) disposed in the displacement stage T is in a staggered pattern or in a grid pattern, but the array of the concave portions 23a (or through-holes 22a) is not limited to such patterns.

More specifically, the plurality of the concave portions may be formed in the placement stage T such that the plurality of depressions 4 in the finally-manufactured cell culture vessel 1 are regularly arrayed to form a predetermined pattern (a decorative pattern or geometric pattern, or characters, a figure, a sign, or the like).

In each of the first embodiment to the fourth embodiment and Modification 1 to Modification 3 described above, the bag-shaped, film-based vessel 1a is used for forming the cell culture vessel, but this is not limitative. The vessel with the depressions therein as manufactured from the bag-shaped, film-based vessel 1a in the present invention can be also used for other applications, for example, as vessels for storing foods or medicines. If these depressions present a predetermined pattern mentioned above, vessels with an artistically high value can be realized.

In each of the embodiments and modifications described above, the manufacturing apparatus for the cell culture vessel may include an observation device (not depicted) such as a camera (imaging device). In the third embodiment, for example, an observation device may be arranged on the placement stage T to observe whether or not depressions have been formed on the bag-shaped, film-based vessel 1a.

If CCD devices or the like are arranged in a plurality of holes disposed in the placement stage T as described above, the behavior of the bag-shaped, film-based vessel 1a can be observed while the bag-shaped, film-based vessel 1a is pressed by the pressing member 21. Here, at least one of the holes in the placement stage T is required to include a CCD device, and the arrangement of CCD devices in all the holes is not necessarily required.

Based on observation results by the observation device as described above, it is possible to control operation of the pressing member 21 and the fluid inlet device 26. As a consequence, the bag-shaped, film-based vessel 1a can be pressed neither excessively nor insufficiently by the pressing member 21. Further, as a consequence, fluid can be introduced into the bag-shaped, film-based vessel 1a neither excessively nor insufficiently at an appropriate supply pressure by the fluid inlet device 26. Moreover, the depressions to be formed in the bag-shaped, film-based vessel 1a can be controlled in size based on the observation results of the observation device.

The above-described observation device is not necessarily needed to be arranged on the side of the placement stage T, but may be arranged on the side of the pressing member 21, for example, if the pressing member 21 is formed from a transparent material such as glass or heat-resistant plastic.

If the placement stage T is formed from the above-described transparent material, the inside of the placement stage T (the conditions of the concave portions) can be observed from the outside of the placement stage T, so that the above-mentioned observation device can be arranged laterally or obliquely of the placement stage T or the pressing member 21.

In the fifth embodiment, for example, it is possible to arrange, on the pressing member 21, an observation device that observes whether or not the bulge shape 12z of the second vessel wall 12 has been formed. By such an observation device, the bulge shape 12z can be appropriately formed by the pressing member 21.

The position of arrangement of the observation device in the fifth embodiment is not limited to the side of the pressing member 21, and the observation device may be arranged at another position, for example, laterally or obliquely of the placement stage 23.

INDUSTRIAL APPLICABILITY

The present invention can be used as a technique for efficiently culturing various cells and also as a technique for manufacturing vessels having good storage performance and high design value.

REFERENCE SIGNS LIST

1 Cell culture vessel
2 Vessel main body
3 Charge/discharge port
4 Depression
10 Cell culture vessel
11 First vessel wall
12 Second vessel wall
13, 14, 15 Charge/discharge port
21 Pressing member
22 Placement stage support member
23 Vessel support member
24 Heating device
25 Drive mechanism
26 Fluid inlet device
27 Suction device
28 Temperature control device
29 Restraint member
T Placement stage
CP Control unit

The invention claimed is:

1. A cell culture vessel comprising:
a first vessel wall as a bottom wall, the first vessel wall having gas permeability;
a second vessel wall disposed in contact with a peripheral edge portion of the first vessel wall, and having a bulge shape protruding relative to the first vessel wall radially inward of the peripheral edge portion; and
a charge/discharge port communicating to a culture space surrounded by the first vessel wall and the bulge shape of the second vessel wall,
wherein the first vessel wall comprises a central section radially inward of the peripheral edge portion,
wherein the entirety of the first vessel wall is flat and the central section of the first vessel wall has a flat film shape so as to form a flat bottom culture surface in the culture space, and
wherein the charge/discharge port has a contact surface where the charge/discharge port is in contact with the first vessel wall, and the contact surface is flush with an inner surface of the first vessel wall.

2. The cell culture vessel according to claim 1, wherein the second vessel wall is flat at a top wall thereof that forms the culture space.

3. The cell culture vessel according to claim 1, wherein the first vessel wall and the second vessel wall have a thickness ratio of substantially 1.

4. The cell culture vessel according to claim 1, wherein the second vessel wall is a film having gas permeability, and
the gas permeability of the first vessel wall and the gas permeability of the second vessel wall are substantially equal to each other.

5. The cell culture vessel according to claim 4, wherein the first vessel wall and the second vessel wall are made from the same material.

6. The cell culture vessel according to claim 1, wherein the first vessel wall and the second vessel wall are parallel to each other at inner surfaces thereof.

7. The cell culture vessel according to claim 1, wherein the charge/discharge port is configured such that the charge/discharge port has a semicircular cross-sectional shape, and has a flat shape at the contact surface where the charge/discharge port is in contact with the first vessel wall, and has a curved shape at a surface where the charge/discharge port is in contact with the second vessel wall.

8. The cell culture vessel according to claim 1, wherein the second vessel wall rises away from the first vessel wall at an end of the charge/discharge port to define the bulge shape of the second vessel wall such that an upwardly extending portion of the second vessel wall is flush with the end of the charge/discharge port.

9. A method for culturing cells by using the cell culture vessel according to claim 1, comprising:
placing the cell culture vessel with the first vessel wall located downward relative to the second vessel wall, and charging cells and culture liquid into the cell culture vessel through the charge/discharge port.

10. A method for manufacturing the cell culture vessel according to claim 1, comprising the steps of:
placing the first vessel wall which is formed of a film having gas permeability, and the second vessel wall which is disposed opposite the first vessel wall, in a superimposed state on a placement stage;
pressing the first vessel wall and the second vessel wall at peripheral edge portions thereof by a restraint member in a state that the second vessel wall is maintained free from being pressed at a central section thereof;
introducing fluid between the first vessel wall and the second vessel wall with the peripheral edge portions thereof pressed by the restraint member; and
heating at least a pressing member while pressing the second vessel wall at the central section thereof by the pressing member.

\* \* \* \* \*